US012358896B2

(12) United States Patent
de Vicente Fidalgo et al.

(10) Patent No.: US 12,358,896 B2
(45) Date of Patent: Jul. 15, 2025

(54) LRRK2 INHIBITORS AND METHODS OF MAKING AND USING THEREOF

(71) Applicant: DENALI THERAPEUTICS INC., South San Francisco, CA (US)

(72) Inventors: Javier de Vicente Fidalgo, Foster City, CA (US); Anthony A. Estrada, San Mateo, CA (US); Jianwen A. Feng, San Mateo, CA (US); Zachary K. Sweeney, Redwood City, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 895 days.

(21) Appl. No.: 17/602,480

(22) PCT Filed: Apr. 10, 2020

(86) PCT No.: PCT/US2020/027742

§ 371 (c)(1),
(2) Date: Oct. 8, 2021

(87) PCT Pub. No.: WO2020/210684

PCT Pub. Date: Oct. 15, 2020

(65) Prior Publication Data

US 2022/0220094 A1 Jul. 14, 2022

Related U.S. Application Data

(60) Provisional application No. 62/832,775, filed on Apr. 11, 2019.

(51) Int. Cl.
*C07D 403/12* (2006.01)

(52) U.S. Cl.
CPC .................................. *C07D 403/12* (2013.01)

(58) Field of Classification Search
CPC .................................................... C07D 403/12
See application file for complete search history.

(56) References Cited

U.S. PATENT DOCUMENTS

2018/0208582 A1 7/2018 Estrada et al.

FOREIGN PATENT DOCUMENTS

EP 2638031 B1 11/2017
WO 2017/218843 A1 12/2017
WO 2018/217946 A1 11/2018
WO 2019/126383 A1 6/2019

OTHER PUBLICATIONS

Zhang et.al. European Journal of Medicinal Chemistry 256 (2023) 115475 (Year: 2023).*
International Search Report and Written Opinion for PCT/US2020/027742 mailed Jun. 29, 2020, 12 pages.
Estrada et al., Discovery of highly potent, selective, and brain-penetrant aminopyrazole leucine-rich repeat kinase 2 (LRRK2) small molecule inhibitors. J Med Chem. Feb. 13, 2014;57(3):921-36.

* cited by examiner

*Primary Examiner* — John S Kenyon
*Assistant Examiner* — Rehana Ismail
(74) *Attorney, Agent, or Firm* — McCarter & English, LLP; Xin Zhang

(57) ABSTRACT

The present disclosure relates generally to LRRK2 inhibitors, or a pharmaceutically acceptable salt, isotopically enriched analog, tautomer, stereoisomer, mixture of stereoisomers, prodrug, or pharmaceutical composition thereof, and methods of making and using thereof.

18 Claims, No Drawings

LRRK2 INHIBITORS AND METHODS OF MAKING AND USING THEREOF

CROSS REFERENCE TO RELATED APPLICATIONS

This application is a 35 U.S.C. § 371 National Stage of International Patent Application No. PCT/US2020/027742, filed Apr. 10, 2020, which claims the benefit under 35 U.S.C. § 119 (e) to U.S. Provisional Application No. 62/832,775, filed Apr. 11, 2019, which are hereby incorporated by reference in their entireties.

FIELD

The present disclosure relates generally to novel heteroaryl-substituted pyrimidines and their use as therapeutic agents, for example, as inhibitors of LRRK2.

DESCRIPTION

Leucine-rich repeat kinase 2 (LRRK2) plays an important role in vesicular trafficking and immune function and has been genetically associated with several human diseases. LRRK2 is a member of the ROCO protein family and shares five conserved domains with all other family members. Many mis-sense mutations to the LRRK2 gene have been linked to autosomal dominant Parkinson's disease in familial studies (Trinh and Farrar, Nature Reviews in Neurology, Vol. 9, 2013, 445-454; Paisan-Ruiz et al., J. Parkinson's Disease, Vol. 3, 2013, 85-103) and to inflammatory bowel diseases (IBDs), such as Crohn's disease (CD) and ulcerative colitis (UC) (Hui et al., Sci. Transl. Med., 2018, 10, 7795).

The most common pathogenic mutation, G2019S, occurs in the highly conserved kinase domain of LRRK2 (See Gilks et al., Lancet, Vol 365, 2005, 415-416). In vitro studies indicate Parkinson's disease-associated mutation leads to increased LRRK2 activity and a decreased rate of GTP hydrolysis (Guo et al., Experimental Cell Research, Vol. 313(16), 2007, 3658-3670). This evidence suggests the kinase and GTPase activities of LRRK2 are important for pathogenesis and the LRRK2 kinase domain may regulate overall LRRK2 function (See Cookson, Nat. Rev. Neurosci., Vol. 11, 2010, 791-797).

The LRRK2 N2081D mutation has been identified as a Crohn's disease risk allele. This mutation is located in the same kinase domain as G2019S and is associated with increased kinase activity like G2019S mutants. The LRRK2 N2081D mutation is also found in some Parkinson's disease patients (Hui et al., Sci. Transl. Med., 2018, 10, 7795). Other studies have linked gastrointestinal inflammation as precursors to brain inflammation and Parkinson's disease (Kishimoto, Y. et. al., Neuromolecular Med. 2019, 21(3): 239-249); Grathwohl, S. et. al., bioRxiv, Dec. 22, 2018-11: 51).

While progress has been made in this field, there remains a need for improved inhibitors of LRRK2 which are useful for treatment of various neurodegenerative diseases, such as Parkinson's disease, Alzheimer's disease and amyotrophic lateral sclerosis, as well as treatment of peripheral disorders, such as inflammatory bowel diseases (IBDs), including Crohn's disease (CD) and ulcerative colitis (UC).

Provided herein are compounds, or a pharmaceutically acceptable salt, isotopically enriched analog, tautomer, stereoisomer, mixture of stereoisomers, or prodrug thereof, that are useful as inhibitors of LRRK2. The disclosure also provides compositions, including pharmaceutical compositions, kits that include the compounds, and methods of using (or administering) and making the compounds, or a pharmaceutically acceptable salt, isotopically enriched analog, tautomer, stereoisomer, mixture of stereoisomers, or prodrug thereof. The disclosure further provides compounds or compositions thereof for use in a method of treating a disease, disorder, or condition that is mediated, at least in part, by LRRK2. Moreover, the disclosure provides uses of the compounds or compositions thereof in the manufacture of a medicament for the treatment of a disease, disorder, or condition that is mediated, at least in part, by LRRK2.

In certain embodiments, provided is a compound of Formula I, or a pharmaceutically acceptable salt, isotopically enriched analog, tautomer, stereoisomer, mixture of stereoisomers, or prodrug thereof.

In another embodiment, provided is a pharmaceutical composition comprising a compound as described in any formula described herein, or a pharmaceutically acceptable salt, isotopically enriched analog, tautomer, stereoisomer, mixture of stereoisomers, or prodrug thereof.

In another embodiment, provided is a method for treating a disease or condition mediated, at least in part, by LRRK2, the method comprising administering an effective amount of the pharmaceutical composition comprising a compound as described in any formula described herein, or a pharmaceutically acceptable salt, isotopically enriched analog, tautomer, stereoisomer, mixture of stereoisomers, or prodrug thereof, and a pharmaceutically acceptable carrier, diluent, or excipient, to a subject in need thereof.

In certain embodiments, the compound is in Table 1 or Table 2, or a pharmaceutically acceptable salt, isotopically enriched analog, tautomer, stereoisomer, mixture of stereoisomers, or prodrug thereof.

In another embodiment, provided is a pharmaceutical composition comprising a compound as shown in Table 1 or Table 2, or a pharmaceutically acceptable salt, isotopically enriched analog, tautomer, stereoisomer, mixture of stereoisomers, or prodrug thereof, and a pharmaceutically acceptable carrier, diluent, or excipient.

In another embodiment, provided is a method for treating a disease or condition mediated, at least in part, by LRRK2, the method comprising administering an effective amount of the pharmaceutical composition comprising a compound as shown in Table 1 or Table 2, or a pharmaceutically acceptable salt, isotopically enriched analog, tautomer, stereoisomer, mixture of stereoisomers, or prodrug thereof, and a pharmaceutically acceptable carrier, diluent, or excipient, to a subject in need thereof.

The description herein sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named. For compound structures, solid/dashed bars represent relative stereochemistry, such as the relative cis- or trans-orientations of two substituents on a ring, while solid/dash wedges depict absolute configuration relative to a plane defined by two solid lines.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In certain embodiments, the term "about" includes the indicated amount ±5%. In certain embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e. $—(CH_2)_3CH_3$), sec-butyl (i.e. $—CH(CH_3)CH_2CH_3$), isobutyl (i.e. $—CH_2CH(CH_3)_2$) and tert-butyl (i.e. $—C(CH_3)_3$); and "propyl" includes n-propyl (i.e. $—(CH_2)_2CH_3$) and isopropyl (i.e. $—CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—." Examples of alkoxy groups include methoxy, ethoxy, n-propoxy, iso-propoxy, n-butoxy, tert-butoxy, sec-butoxy, n-pentoxy, n-hexoxy and 1,2-dimethylbutoxy.

"Alkoxyalkyl" refers to the group "alkyl-O-alkyl."

"Alkylthio" refers to the group "alkyl-S—."

"Alkylsulfinyl" refers to the group "alkyl-S(O)—."

"Alkylsulfonyl" refers to the group "alkyl-$S(O)_2$—."

"Alkylsulfonylalkyl" refers to -alkyl-$S(O)_2$-alkyl.

"Acyl" refers to a group —$C(O)R^y$, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —$C(O)NR^yR^z$ and an "N-amido" group which refers to the group —$NR^yC(O)R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amidoalkyl" refers to refers to an alkyl group as defined above, wherein one or more hydrogen atoms are replaced by an amido group.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aminoalkyl" refers to the group "-alkyl-$NR^yR^z$," wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —$C(NR^y)(NR^z_2)$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g. monocyclic) or multiple rings (e.g. bicyclic ortricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-."

"Carbamoyl" refers to both an "O-carbamoyl" group which refers to the group —O—$C(O)NR^yR^z$ and an "N-carbamoyl" group which refers to the group —$NR^yC(O)OR^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —$OC(O)R^x$ and —$C(O)OR^x$, wherein $R^x$ is alkyl, alkenyl, alkynyl, cycloalkyl, heterocyclyl, aryl, heteroalkyl, or heteroaryl; each of which may be optionally substituted, as defined herein.

"Cyanoalkyl" refers to refers to an alkyl group as defined above, wherein one or more (e.g., one to three) hydrogen atoms are replaced by a cyano group.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e. the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkoxy" refers to "—O-cycloalkyl."

"Cycloalkylalkyl" refers to the group "cycloalkyl-alkyl-."

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Haloalkyl" refers to an unbranched or branched alkyl group as defined above, wherein one or more hydrogen atoms (e.g., one to three) are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms (e.g., one to three) are replaced by a halogen.

"Hydroxyalkyl" refers to an alkyl group as defined above, wherein one or more hydrogen atoms (e.g., one to three) are replaced by a hydroxy group.

"Heteroalkyl" refers to an alkyl group in which one or more (e.g., one to three) of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2, or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.), and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-."

"Heterocyclyl" refers to a saturated or partially unsaturated cyclic alkyl group, with one or more (e.g., one to three) ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (=O) or N-oxide ($—O^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e. thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene) sulfonyloxy, and the like.

"Oxime" refers to the group $—CR^y(=NOH)$ wherein $R^y$ is hydrogen, alkyl, alkenyl, alkynyl, cycloalkyl, heterocyclyl, aryl, heteroalkyl, or heteroaryl; each of which may be optionally substituted, as defined herein.

"Sulfonyl" refers to the group $—S(O)_2R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group $—S(O)R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups $—SO_2NR^yR^z$ and $—NR^ySO_2R^z$, where $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., one to five or one to three) hydrogen atoms on the designated atom or group may or may not be replaced by a moiety other than hydrogen.

The term "substituted" used herein means any of the above groups (e.g., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or $—Si(R^y)_3$ wherein each $R^y$ is independently hydrogen, alkyl, alkenyl, alkynyl, heteroalkyl, cycloalkyl, aryl, heteroaryl, or heterocyclyl.

In certain embodiments, "substituted" includes any of the above groups (e.g., alkyl, alkenyl, alkynyl, alkylene, alkoxy, haloalkyl, haloalkoxy, cycloalkyl, aryl, heterocyclyl, heteroaryl, and/or heteroalkyl) in which one or more (e.g., one to five or one to three) hydrogen atoms are replaced with $—NR^gR^h$, $—NR^gC(=O)R^h$, $—NR^gC(=O)NR^gR^h$, $—NR^gC(=O)OR^h$, $—NR^gSO_2R^h$, $—OC(=O)NR^gR^h$, $—OR^g$, $—SR^g$, $—SOR^g$, $—SO_2R^g$, $—OSO_2R^g$, $—SO_2OR^g$, $=NSO_2R^g$, and $—S_2NR^gR^h$. "Substituted" also means any of the above groups in which one or more (e.g., one to five or one to three) hydrogen atoms are replaced with $—C(=O)R^g$, $—C(=O)OR^g$, $—C(=O)NR^gR^h$, $—CH_2SO_2R^g$, $—CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. "Substituted" further means any of the above groups in which one or more (e.g., one to five or one to three) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In addition, each of the foregoing substituents may also be optionally substituted with one or more (e.g., one to five or one to three) of the above substituents. In certain embodiments, the term "substituted" means that any one or more hydrogen atoms on the designated atom or group is replaced with one or more substituents other than hydrogen, provided that a designated atom's normal valence on the group is not exceeded.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, In certain embodiments, the term "substituted alkyl" refers to an alkyl group having one or more (e.g., one to five or one to three) substituents including hydroxy, halo, alkoxy, acyl, oxo, amino, cycloalkyl, heterocyclyl, aryl and heteroaryl. In certain embodiments, the one or more (e.g., one to five or one to three) substituents may be further substituted with halo, alkyl, haloalkyl, hydroxy, alkoxy, cycloalkyl, heterocyclyl, aryl, or heteroaryl, each of which is substituted. In certain embodiments, the substituents may be further substituted with halo, alkyl, haloalkyl, alkoxy, hydroxy, cycloalkyl, heterocyclyl, aryl, or heteroaryl, each of which is unsubstituted.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{4}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$, and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino, and/or carboxyl groups, or groups similar thereto.

Provided are also or a pharmaceutically acceptable salt, isotopically enriched analog, deuterated analog, stereoisomer, mixture of stereoisomers, and prodrugs of the compounds described herein. "Pharmaceutically acceptable" or "physiologically acceptable" refer to compounds, salts, compositions, dosage forms, and other materials which are useful in preparing a pharmaceutical composition that is suitable for veterinary or human pharmaceutical use. In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$ (substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. Compounds

Provided herein are compounds, or a pharmaceutically acceptable salt, isotopically enriched analog, tautomer, stereoisomer, mixture of stereoisomers, or prodrug thereof, that are useful as inhibitors of LRRK2.

In one embodiment, provided is a compound of Formula I:

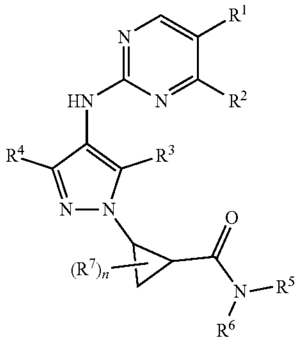

I or a pharmaceutically acceptable salt, isotopically enriched analog, tautomer, stereoisomer, mixture of stereoisomers, or prodrug thereof, wherein:

n is 0, 1, 2, or 3;

$R^1$ is halo, cyano, $C_{1-6}$ alkyl, $C_{1-6}$ alkenyl, $C_{1-6}$ alkynyl, cycloalkyl, $C_{1-6}$ alkoxy, cycloalkoxy, $C_{1-6}$ alkylthio, $C_{1-6}$ alkylsulfonyl, —C(O)$R^{10}$, or —C(O)N($R^{11}$)($R^{12}$), wherein each $C_{1-6}$ alkyl, $C_{1-6}$ alkenyl, $C_{1-6}$ alkynyl, cycloalkyl, $C_{1-6}$ alkoxy, cycloalkoxy, $C_{1-6}$ alkylthio, and $C_{1-6}$ alkylsulfonyl is independently optionally substituted;

$R^2$ is $C_{1-6}$ alkoxy, cycloalkyl, cycloalkoxy, $C_{1-6}$ alkylthio, $C_{1-6}$ alkylsulfonyl, or —N($R^{11}$)($R^{11}$) wherein each $C_{1-6}$ alkoxy, cycloalkyl, cycloalkoxy, $C_{1-6}$ alkylthio, and $C_{1-6}$ alkylsulfonyl is independently optionally substituted;

$R^3$ is hydrogen or halo;

$R^4$ is hydrogen, halo, cyano, $C_{1-6}$ alkyl, $C_{1-6}$ alkenyl, $C_{1-6}$ alkynyl, cycloalkyl, heterocyclyl, heteroaryl, $C_{1-6}$ alkylthio, $C_{1-6}$ alkylsulfonyl, —C(O)$R^{10}$, or —C(O)N($R^{11}$)($R^{12}$), wherein each $C_{1-6}$ alkyl, $C_{1-6}$ alkenyl, $C_{1-6}$ alkynyl, cycloalkyl, heterocyclyl, heteroaryl, $C_{1-6}$ alkylthio, and $C_{1-6}$ alkylsulfonyl is independently optionally substituted;

$R^5$ and $R^6$ are each independently hydrogen, $C_{1-6}$ alkyl or cycloalkyl, or $R^5$ and $R^6$ together form a heterocyclyl, wherein each $C_{1-6}$ alkyl, cycloalkyl, and heterocyclyl is independently optionally substituted;

$R^7$ is halo or $C_{1-6}$ alkyl, wherein each $C_{1-6}$ alkyl is independently optionally substituted;

each $R^{10}$ is independently $C_{1-6}$ alkyl or $C_{1-6}$ alkoxy, wherein each $C_{1-6}$ alkyl and $C_{1-6}$ alkoxy is independently optionally substituted;

each $R^{11}$ and $R^{12}$ are independently hydrogen, $C_{1-6}$ alkyl, cycloalkyl, or $R^{11}$ and $R^{12}$ together form an heterocyclyl group, wherein each $C_{1-6}$ alkyl, cycloalkyl, and heterocyclyl is independently optionally substituted; and $R^{13}$ and $R^{14}$ are each independently hydrogen, $C_{1-6}$ alkyl, cycloalkyl, or $R^{13}$ and $R^{14}$ together form a heterocyclyl, wherein each $C_{1-6}$ alkyl, cycloalkyl, and heterocyclyl is independently optionally substituted.

In certain embodiments, $R^2$ is optionally substituted $C_{1-6}$ alkoxy, optionally substituted cycloalkyl, or —N($R^{13}$)($R^{14}$).

In certain embodiments, $R^2$ is —N($R^{13}$)($R^{14}$).

In certain embodiments, $R^2$ is —N($R^{13}$)($R^{14}$), and $R^{13}$ and $R^{14}$ are each independently hydrogen, optionally substituted $C_{1-6}$ alkyl, or optionally substituted cycloalkyl.

In certain embodiments, $R^2$ is —N($R^{13}$)($R^{14}$), $R^{13}$ is hydrogen and $R^{14}$ is hydrogen, optionally substituted $C_{1-6}$ alkyl, or optionally substituted cycloalkyl.

In certain embodiments, $R^2$ is cyclopropylamino, (1-methylcyclopropyl)amino, —NH($CH_3$), or —NH($CH_2CH_3$).

In certain embodiments, $R^2$ is —NH($CH_3$) or —NH($CH_2CH_3$).

In certain embodiments, $R^2$ is cyclopropylamino or (1-methylcyclopropyl)amino.

In certain embodiments, provided is a compound of Formula I:

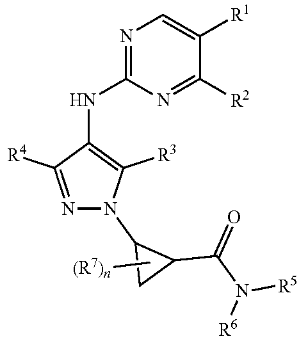

I or a pharmaceutically acceptable salt, isotopically enriched analog, tautomer, stereoisomer, mixture of stereoisomers, or prodrug thereof, wherein:

n is 0, 1, 2, or 3;

$R^1$ is halo, cyano, or $C_{1-6}$ alkyl optionally substituted with one or more halo;

$R^2$ is —N($R^{13}$)($R^{14}$), where $R^{13}$ is hydrogen and $R^{14}$ is hydrogen, $C_{1-6}$ alkyl, or cycloalkyl;

$R^3$ is hydrogen or halo;

$R^4$ is methyl or cycloalkyl;

$R^5$ and $R^6$ are each independently hydrogen, $C_{1-6}$ alkyl or cycloalkyl; and $R^7$ is halo or $C_{1-6}$ alkyl.

In certain embodiments, provided is a compound of Formula I, or a pharmaceutically acceptable salt, isotopically enriched analog, tautomer, stereoisomer, mixture of stereoisomers, or prodrug thereof, wherein:

n is 0;

$R^1$ is halo, cyano, or $C_{1-6}$ alkyl optionally substituted with one or more halo;

$R^2$ is —N($R^{13}$)($R^{14}$), where $R^{13}$ is hydrogen and $R^{14}$ is hydrogen, $C_{1-6}$ alkyl, or cycloalkyl;

$R^3$ is hydrogen or halo;

$R^4$ is methyl or cycloalkyl; and $R^5$ and $R^6$ are each independently hydrogen, $C_{1-6}$ alkyl or cycloalkyl.

In certain embodiments, provided is a compound of Formula IA:

IA

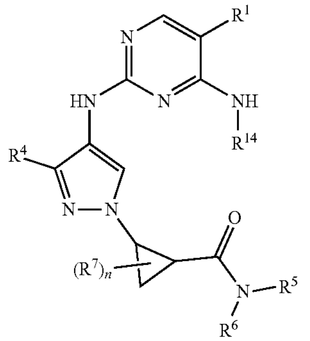

or a pharmaceutically acceptable salt, isotopically enriched analog, tautomer, stereoisomer, mixture of stereoisomers, or prodrug thereof, wherein:

n is 0, 1, 2, or 3;

$R^1$ is halo or optionally substituted $C_{1-6}$ alkyl;

$R^4$ is hydrogen, halo, cyano, $C_{1-6}$ alkyl, $C_{1-6}$ alkenyl, $C_{1-6}$ alkynyl, cycloalkyl, heterocyclyl, heteroaryl, $C_{1-6}$ alkylthio, $C_{1-6}$ alkylsulfonyl, —C(O)$R^{10}$, or —C(O)N($R^{11}$)($R^{12}$), wherein each $C_{1-6}$ alkyl, $C_{1-6}$ alkenyl, $C_{1-6}$ alkynyl, cycloalkyl, heterocyclyl, heteroaryl, $C_{1-6}$ alkylthio, and $C_{1-6}$ alkylsulfonyl is independently optionally substituted;

$R^5$ and $R^6$ are each independently hydrogen, $C_{1-6}$ alkyl or cycloalkyl, or $R^5$ and $R^6$ together form a heterocyclyl, wherein each $C_{1-6}$ alkyl, cycloalkyl, and heterocyclyl is independently optionally substituted;

$R^7$ is halo or $C_{1-6}$ alkyl, wherein each $C_{1-6}$ alkyl is independently optionally substituted;

each $R^{10}$ is independently $C_{1-6}$ alkyl or $C_{1-6}$ alkoxy, wherein each $C_{1-6}$ alkyl and $C_{1-6}$ alkoxy is independently optionally substituted;

each $R^{11}$ and $R^{12}$ are independently hydrogen, $C_{1-6}$ alkyl, cycloalkyl, or $R^{11}$ and $R^{12}$ together form an heterocyclyl group, wherein each $C_{1-6}$ alkyl, cycloalkyl, and heterocyclyl is independently optionally substituted; and $R^{14}$ is $C_{1-6}$ alkyl or cycloalkyl, wherein each $C_{1-6}$ alkyl and cycloalkyl is independently optionally substituted.

In certain embodiments, $R^4$ is other than optionally substituted cycloalkyl.

In certain embodiments, $R^4$ is methyl.

In certain embodiments, n is 0.

In certain embodiments, n is 1.

In certain embodiments, n is 1 or 2.

In certain embodiments, n is 0 or 1.

In certain embodiments, $R^7$ is optionally substituted $C_{1-6}$ alkyl.

In certain embodiments, $R^7$ is halo.

In one embodiment, provided is a compound of Formula IB:

IB

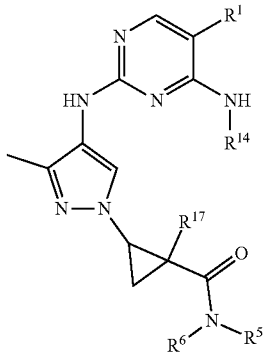

or a pharmaceutically acceptable salt, isotopically enriched analog, tautomer, stereoisomer, mixture of stereoisomers, or prodrug thereof, wherein:

$R^1$ is halo or optionally substituted $C_{1-6}$ alkyl;

$R^5$ and $R^6$ are each independently hydrogen, $C_{1-6}$ alkyl or cycloalkyl, or $R^5$ and $R^6$ together form a heterocyclyl, wherein each $C_{1-6}$ alkyl, cycloalkyl, and heterocyclyl is independently optionally substituted;

$R^{14}$ is $C_{1-6}$ alkyl or cycloalkyl, wherein each $C_{1-6}$ alkyl and cycloalkyl is independently optionally substituted; and $R^{17}$ is hydrogen, halo or optionally substituted $C_{1-6}$ alkyl.

In one embodiment, provided is a compound of Formula IC:

IC

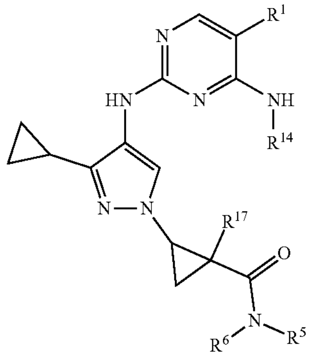

or a pharmaceutically acceptable salt, isotopically enriched analog, tautomer, stereoisomer, mixture of stereoisomers, or prodrug thereof, wherein:

$R^1$ is halo or optionally substituted $C_{1-6}$ alkyl;

$R^5$ and $R^6$ are each independently hydrogen, $C_{1-6}$ alkyl or cycloalkyl, or $R^5$ and $R^6$ together form a heterocyclyl, wherein each $C_{1-6}$ alkyl, cycloalkyl, and heterocyclyl is independently optionally substituted;

$R^{14}$ is $C_{1-6}$ alkyl or cycloalkyl, wherein each $C_{1-6}$ alkyl and cycloalkyl is independently optionally substituted; and $R^{17}$ is hydrogen, halo or optionally substituted $C_{1-6}$ alkyl.

In certain embodiments, $R^1$ is halo, cyano, or optionally substituted $C_{1-6}$ alkyl.

In certain embodiments, $R^1$ is halo, cyano, or $C_{1-6}$ alkyl optionally substituted with one or more halo.

In certain embodiments, $R^1$ is halo, cyano, or $C_{1-6}$ alkyl optionally substituted with one to five halo.

In certain embodiments, $R^1$ is halo, cyano, or $C_{1-6}$ alkyl optionally substituted with one to three halo.

In certain embodiments, $R^1$ is halo.

In certain embodiments, $R^1$ is bromo.

In certain embodiments, $R^1$ is optionally substituted $C_{1-6}$ alkyl.

In certain embodiments, $R^1$ is $C_{1-6}$ alkyl optionally substituted with one or more halo.

In certain embodiments, $R^1$ is $C_{1-6}$ alkyl optionally substituted with one to five halo.

In certain embodiments, $R^1$ is $C_{1-6}$ alkyl optionally substituted with one to three halo.

In certain embodiments, $R^1$ is $C_{1-6}$ haloalkyl.

In certain embodiments, $R^1$ is $—CF_3$.

In certain embodiments, $R^{14}$ is optionally substituted $C_{1-6}$ alkyl.

In certain embodiments, $R^{14}$ is $C_{1-6}$ alkyl.

In certain embodiments, $R^{14}$ is methyl or ethyl.

In certain embodiments, $R^{14}$ is optionally substituted cycloalkyl.

In certain embodiments, $R^{14}$ is cycloalkyl.

In certain embodiments, $R^{14}$ is cyclopropyl.

In certain embodiments, $R^{17}$ is methylcyclopropyl.

In certain embodiments, $R^{17}$ is hydrogen.

In certain embodiments, $R^{17}$ is halo.

In certain embodiments, $R^{17}$ is optionally substituted $C_{1-6}$ alkyl.

In certain embodiments, $R^{17}$ is $C_{1-6}$ alkyl.

In certain embodiments, $R^{17}$ is methyl.

In certain embodiments, provided is a compound as shown in Table 1 or a pharmaceutically acceptable salt, isotopically enriched analog, tautomer, stereoisomer, mixture of stereoisomers, or prodrug thereof.

TABLE 1

| No. | STRUCTURE |
|---|---|
| 1 | 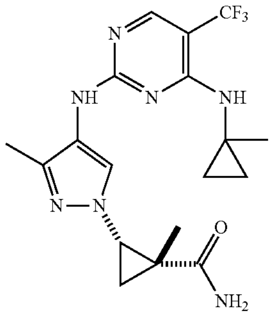 |
| 2 | 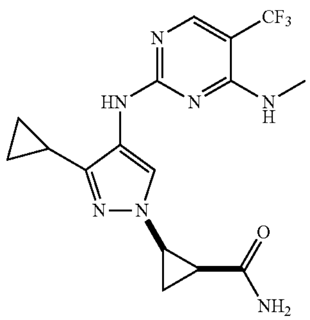 |

TABLE 1-continued

| No. | STRUCTURE |
|---|---|
| 3 | 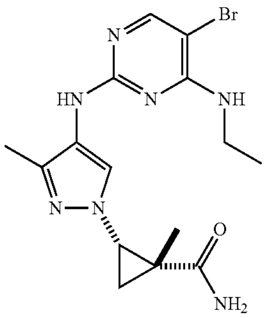 |
| 4 | 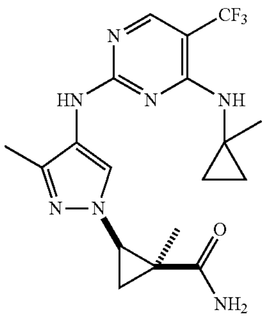 |
| 5 | 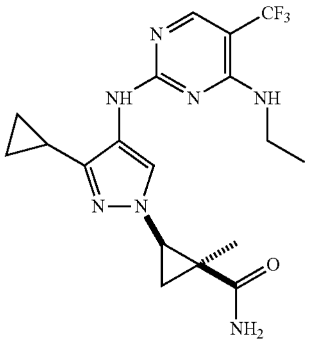 |
| 6 | 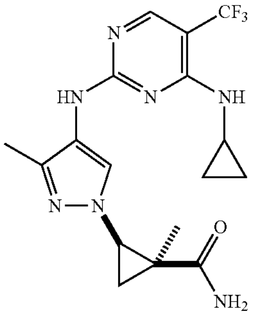 |

TABLE 1-continued

| No. | STRUCTURE |
|---|---|
| 7 | 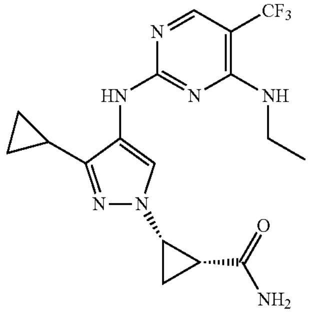 [SMILES: CCNc1nc(Nc2cn([C@H]3C[C@H]3C(N)=O)nc2C2CC2)ncc1C(F)(F)F] |
| 8 | 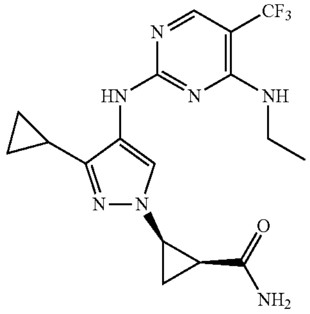 [SMILES: CCNc1nc(Nc2cn([C@@H]3C[C@@H]3C(N)=O)nc2C2CC2)ncc1C(F)(F)F] |

In certain embodiments, a compound may be selected from those compounds in Table 1. Also included within the disclosure are pharmaceutically acceptable salts, deuterated analogs, tautomers, stereoisomers, mixture of stereoisomers, or prodrug of a compound of the disclosure. In certain embodiments, provided are compounds of Table 1 for use in the methods described herein.

Specific stereoisomers contemplated include the following in Table 2.

TABLE 2

| STRUCTURE |
|---|
| 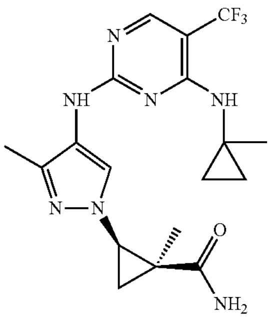 |

TABLE 2-continued

| STRUCTURE |
|---|
| 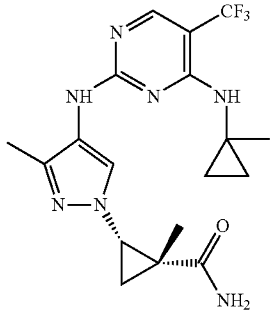 |
| 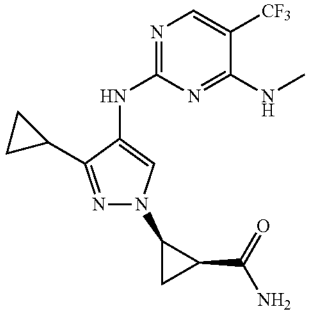 [SMILES: CNc1nc(Nc2cn([C@@H]3C[C@@H]3C(N)=O)nc2C2CC2)ncc1C(F)(F)F] |
| 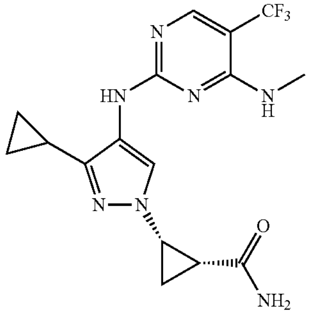 [SMILES: CNc1nc(Nc2cn([C@H]3C[C@H]3C(N)=O)nc2C2CC2)ncc1C(F)(F)F] |
| 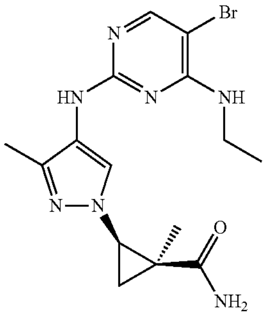 [SMILES: CCNc1nc(Nc2cn([C@@H]3C[C@]3(C)C(N)=O)nc2C)ncc1Br] |
| 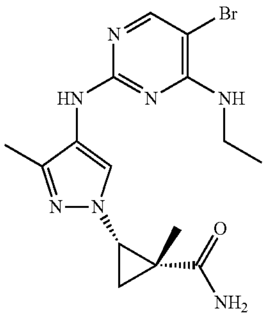 [SMILES: CCNc1nc(Nc2cn([C@H]3C[C@@]3(C)C(N)=O)nc2C)ncc1Br] |

TABLE 2-continued

| STRUCTURE |
| --- |
| 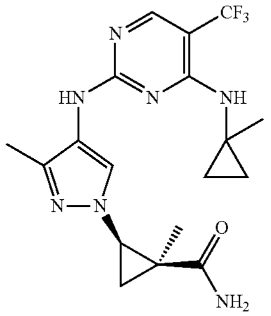 |
| 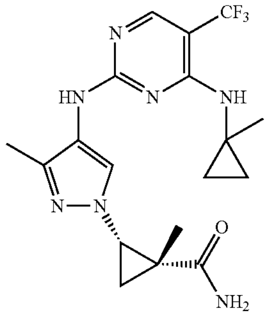 |
| 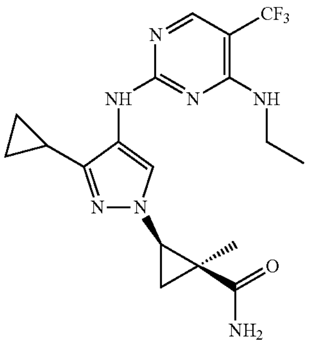 [SMILES: CCNc1nc(Nc2cn([C@@H]3C[C@]3(C)C(N)=O)nc2C2CC2)ncc1C(F)(F)F] |
| 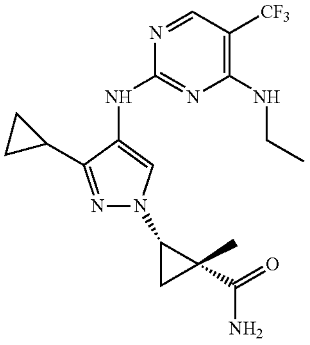 [SMILES: CCNc1nc(Nc2cn([C@H]3C[C@@]3(C)C(N)=O)nc2C2CC2)ncc1C(F)(F)F] |

TABLE 2-continued

| STRUCTURE |
| --- |
| 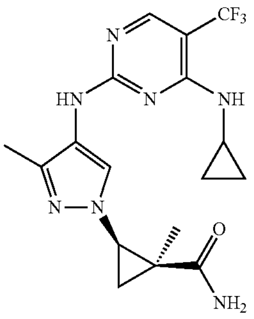 [SMILES: Cc1nn([C@@H]2C[C@]2(C)C(N)=O)cc1Nc1ncc(C(F)(F)F)c(NC2CC2)n1] |
| 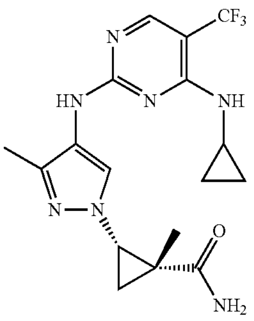 [SMILES: Cc1nn([C@H]2C[C@@]2(C)C(N)=O)cc1Nc1ncc(C(F)(F)F)c(NC2CC2)n1] |
| 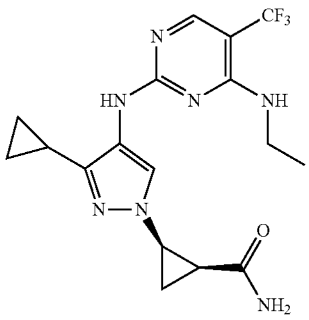 [SMILES: CCNc1nc(Nc2cn([C@@H]3C[C@@H]3C(N)=O)nc2C2CC2)ncc1C(F)(F)F] |
| 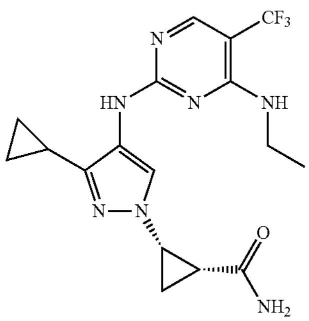 [SMILES: CCNc1nc(Nc2cn([C@H]3C[C@H]3C(N)=O)nc2C2CC2)ncc1C(F)(F)F] |

In certain embodiments, a compound may be selected from those compounds in Table 2. Also included within the disclosure are pharmaceutically acceptable salts, deuterated analogs, tautomers, stereoisomers, mixture of stereoisomers, or prodrug thereof. In certain embodiments, provided are compounds of Table 2 for use in the methods described herein.

3. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival.

"Prevention" or "preventing" means any treatment of a disease or condition that causes the clinical symptoms of the disease or condition not to develop. Compounds may, in certain embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In certain embodiments, the subject is a mammal. In certain embodiments, the subject is a human.

The term "therapeutically effective amount" or "effective amount" of a compound described herein or a pharmaceutically acceptable salt, isotopically enriched analog, tautomer, stereoisomer, mixture of stereoisomers, or prodrug thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

LRRK2 has been associated with the transition from mild cognitive impairment to Alzheimer's disease; L-Dopa induced dyskinesia (Hurley et al., Eur. J, Neurosci., Vol. 26, 2007, 171-177); CNS disorders associated with neuroprogenitor cell proliferation and migration, and regulation of LRRK2 may have utility in improving neurological outcomes following ischemic injury, and stimulating restoration of CNS function following neuronal injury such as ischemic stroke, traumatic brain injury, or spinal cord injury (Milosevic et al., Neurodegen., Vol. 4, 2009, 25; See Zhang et al., J. Neurosci. Res. Vol. 88, 2010, 3275-3281); Parkinson's disease, Alzheimer's disease, multiple sclerosis, and HIV-induced dementia (See Milosevic et al., Mol. Neurodegen., Vol. 4, 2009, 25); kidney, breast, prostate (e.g. solid tumor), blood and lung cancer, and acute myeologenouse leukemia (AML); lymphomas and leukemias (See Ray et al., J. Immunolo., Vol. 230, 2011, 109); multiple myeloma (Chapman et al., Nature, Vol. 471, 2011, 467-472); papillary renal and thyroid carcinomas; multiple myeloma (Chapman et al., Nature, Vol. 471, 2011, 467-472); diseases of the immune system, including rheumatoid arthritis, systemic lupus erythematosus autoimmune hemolytic anemia, pure red cell aplasia, idiopathic thrombocytopenic pupura (ITP), Evans syndrome, vasculitis, bullous skin disorders, type 1 diabetes mellitus, Sjogren's syndrome, Delvic's disease, and inflammatory myopathies (Nakamura et al., DNA Res. Vol. 13(4), 2006, 169-183; See Engel et al., Pharmacol. Rev. Vol. 63, 2011, 127-156; Homam et al., J. Clin. Neuromuscular Disease, Vol. 12, 2010, 91-102); ankylosing spondylitis and leprosy infection (Danoy et al., PLoS Genetics, Vol. 6(12), 2010, e1001195, 1-5; see Zhang et al., N. Eng. J. Med. Vol. 361, 2009, 2609-2618); alpha-synucleinopathies, taupathies (See Li et al., 2010 Neurodegen. Dis. Vol. 7, 2010, 265-271); Gaucher disease (See Westbroek et al., Trends. Mol. Med. Vol. 17, 2011, 485-493); tauopathy diseases characterized by hyperphosphorylation of Tau such as argyrophilic grain disease, Pick's disease, corticobasal degeneration, progressive supranuclear palsy, and inherited frontotemporal dementia and parkinsonism linked to chromosome 17 (See Goedert, M and Jakes, R, Biochemica et Biophysica Acta, Vol. 1739, 2005, 240-250); diseases characterized by diminished dopamine levels such as withdrawal symptoms/relapse associated with drug addiction (See Rothman et al., Prog. Brain Res., Vol. 172, 2008, 385); microglial proinflammatory responses (See Moehle et al., J. Neuroscience Vol. 32, 2012, 1602-1611); Crohn's disease pathogenesis (see Barrett et al., Nature Genetics, Vol. 40, 2008, 955-962); and amyotrophic lateral sclerosis (ALS).

Increased LRRK2 activity may also be characteristic of ALS. Significantly elevated levels of LRRK2 mRNA have been observed in fibroblasts of Niemann-Pick Type C (NPC) disease patients, indicating abnormal LRRK2 function may play a role in lysosomal disorders.

In another aspect, the present disclosure relates to a method of treating a disease or condition mediated, at least in part, by LRRK2. In particular, the disclosure provides methods for preventing or treating a disorder associated with LRRK2 in a mammal, comprising the step of administering to said mammal a therapeutically effective amount of a compound as described herein (e.g., a Compound of Formula I, a compound of Table 1 or Table 2, etc.), a pharmaceutically acceptable salt, isotopically enriched analog, tautomer, stereoisomer, mixture of stereoisomers, or prodrug thereof, or a therapeutic preparation of the present disclosure.

In certain embodiments, the disease or condition mediated, at least in part, by LRRK2 is a neurodegenerative disease, for example, a central nervous system (CNS) disorder, such as Parkinson's disease (PD), Alzheimer's disease (AD), dementia (including Lewy body dementia and vascular dementia), amyotrophic lateral sclerosis (ALS), age related memory dysfunction, mild cognitive impairment (e.g., including the transition from mild cognitive impairment to Alzheimer's disease), argyrophilic grain disease, lysosomal disorders (for example, Niemann-Pick Type C disease, Gaucher disease) corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Huntington's disease (HD), and HIV-associated dementia (HAD). In certain embodiments, the disorder is an ischemic disease of organs including but not limited to brain, heart, kidney, and liver.

While not being bound by treatment mechanism, in some embodiments LRRK2 inhibitors, such as those that do not cross the blood brain barrier, can suppress peripheral inflammation that trigger brain inflammation, thereby treating CNS diseases such as Parkinson's disease. The peripheral inflammation can include, for example, gut inflammation (Kishimoto, Y. et. al., Neuromolecular Med. 2019, 21(3): 239-249).

In some other embodiments, the disease or condition mediated, at least in part, by LRRK2 is cancer. In certain specific embodiments, the cancer is thyroid, renal (including papillary renal), breast, lung, blood, and prostate cancers (e.g. solid tumor), leukemias (including acute myelogenous leukemia (AML)), or lymphomas. In certain embodiments, the cancer is kidney cancer, breast cancer, prostate cancer, blood cancer, papillary cancer, lung cancer, acute myelogenous leukemia, or multiple myeloma.

In certain embodiments, a compound as disclosed herein, or a pharmaceutically acceptable salt, isotopically enriched analog, tautomer, stereoisomer, mixture of stereoisomers, or prodrug thereof, is used for treatment of inflammatory disorders. In certain embodiments, the disorder is an inflammatory disease of the intestines, such as Crohn's disease or ulcerative colitis (both generally known together as inflammatory bowel disease). In certain embodiments, the inflammatory disease is leprosy, amyotrophic lateral sclerosis, rheumatoid arthritis, or ankylosing spondylitis. In certain embodiments, the inflammatory disease is leprosy, Crohn's disease, inflammatory bowel disease, ulcerative colitis, amyotrophic lateral sclerosis, rheumatoid arthritis, or ankylosing spondylitis. In certain embodiments, the inflammatory disease is leprosy. In certain embodiments, the inflammatory disease is Crohn's disease. In certain embodiments, the inflammatory disease is inflammatory bowel disease. In certain embodiments, the inflammatory disease is ulcerative colitis. In certain embodiments, the inflammatory disease is amyotrophic lateral sclerosis. In certain embodiments, the inflammatory disease is rheumatoid arthritis. In certain embodiments, the inflammatory disease ankylosing spondylitis.

In certain embodiments, a compound disclosed herein, a pharmaceutically acceptable salt, isotopically enriched analog, tautomer, stereoisomer, mixture of stereoisomers, or prodrug thereof, is used in methods for treatment of multiple sclerosis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease, and inflammatory myopathies.

In certain embodiments, a compound as disclosed herein, a pharmaceutically acceptable salt, isotopically enriched analog, tautomer, stereoisomer, mixture of stereoisomers, or prodrug thereof, or composition as disclosed herein is used in methods for treatment of tuberculosis.

In certain embodiments, the present disclosure relates to a method of treating a lysosomal storage disorder comprising administering an effective amount of a compound, or a pharmaceutically acceptable salt, isotopically enriched analog, tautomer, stereoisomer, mixture of stereoisomers, or prodrug thereof, or a composition as disclosed herein, to a subject in need thereof. In certain embodiments, the disorder is Niemann-Pick Type A, Niemann-Pick Type B, and Niemann-Pick Type C, Gaucher Type I, Gaucher Type II, Gaucher Type III, Hurler (MPS I), Hunter (MPS II), Sanfilippo A, Sanfilippo B, Sanfilippo C, Sanfilippo D, Sly (MPS VII), Pompe, Mucolipidosis IV, Multiple sulfatase deficiency, GM1 Gangliosidosis, GM2 Gangliosidosis AB variant, GM2 Gangliosidosis (Tay-Sachs), GM2 Gangliosidosis (Sandhoff), α-Mannosidosis, β-Mannosidosis, α-Fucosidosis, Sialidosis, I-cell disease (MLII), Pseudo-Hurler polydystrophy (ML III), Farber, Aspartylglycosaminuria, Krabbe, Cystinosis, Salla disease, Wolman, Schindler-Kanzaki, Galactosialidosis, Pyknodysostosis, Batten (CLN1-10), Danon, Chediak-Higashi, Griscelli, Fabry, Hermansky-Pudliak, Maroteaux-Lamy (MPS VI), Hyaluronidase deficiency (MPS IX), Cholesterol ester storage disease, Morquio A or Morquio B.

In certain embodiments, the present disclosure relates to a method of treating an autophagy-related disorder comprising administering an effective amount of a comprising administering an effective amount of a compound, or a pharmaceutically acceptable salt, isotopically enriched analog, tautomer, stereoisomer, mixture of stereoisomers, or prodrug thereof, or a composition as disclosed herein, to a subject in need thereof. In certain embodiments, the disorder is Crohn's disease, Parkinson's disease, Ulcerative colitis, ALS, Systemic lupus erythematosus, Childhood ataxia, Systemic sclerosis, Hereditary spastic paraparesis type 15, Static encephalopathy of childhood with neurodegeneration in adulthood (SENDA), or Vici syndrome)

Other embodiments include methods for enhancing cognitive memory of a subject, the method comprising administering an effective amount of a compound, or a pharmaceutically acceptable salt, isotopically enriched analog, tautomer, stereoisomer, mixture of stereoisomers, or prodrug thereof, or a composition comprising the compound, or a pharmaceutically acceptable salt, isotopically enriched analog, tautomer, stereoisomer, mixture of stereoisomers, or prodrug thereof, as described herein to a subject in need thereof.

In certain embodiments, provided is a method for preventing or treating a disorder associated with LRRK2 in a mammal, comprising the step of administering to said mammal a therapeutically effective amount of compound 7, or a pharmaceutically acceptable salt, isotopically enriched analog, tautomer, or prodrug thereof, or a pharmaceutical composition comprising the same.

In certain embodiments, provided is a method for preventing or treating Crohn's disease in a mammal, comprising the step of administering to said mammal a therapeutically effective amount of compound 7, or a pharmaceutically acceptable salt, isotopically enriched analog, tautomer, or prodrug thereof, or a pharmaceutical composition comprising the same.

In certain embodiments, provided is a method for preventing or treating inflammatory bowel disease in a mammal, comprising the step of administering to said mammal a therapeutically effective amount of compound 7, or a pharmaceutically acceptable salt, isotopically enriched analog, tautomer, or prodrug thereof, or a pharmaceutical composition comprising the same.

In certain embodiments, provided is a method for preventing or treating ulcerative colitis in a mammal, comprising the step of administering to said mammal a therapeutically effective amount of compound 7, or a pharmaceutically acceptable salt, isotopically enriched analog, tautomer, or prodrug thereof, or a pharmaceutical composition comprising the same.

Other embodiments include use of a compound disclosed herein in therapy. Some embodiments include their use in the treatment of a neurodegenerative disease, cancer, or an inflammatory disease.

In certain embodiments, provided is a compound, or a pharmaceutically acceptable salt, isotopically enriched analog, tautomer, stereoisomer, mixture of stereoisomers, or prodrug thereof, for use in the treatment of Alzheimer's disease, L-Dopa induced dyskinesia, Parkinson's disease, dementia, ALS, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

In certain embodiments, provided is the use of a compound, or a pharmaceutically acceptable salt, isotopically enriched analog, tautomer, stereoisomer, mixture of stereoisomers, or prodrug thereof, disclosed herein for the manufacture of a medicament for treating a neurodegenerative disease, cancer, or an inflammatory disease.

In certain embodiments, provided is the use of a compound or a pharmaceutically acceptable salt, isotopically enriched analog, tautomer, stereoisomer, mixture of stereoisomers, or prodrug thereof, as disclosed herein for the manufacture of a medicament for treating Alzheimer's disease, L-Dopa induced dyskinesia, Parkinson's disease, dementia, amyotrophic lateral sclerosis, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

In certain embodiments, the present disclosure relates to a compound, or a pharmaceutically acceptable salt, isotopically enriched analog, tautomer, stereoisomer, mixture of stereoisomers, or prodrug thereof, for inhibiting cell death, wherein the compounds are as described herein (e.g., Table 1 or Table 2). In certain embodiments, the compounds of the present disclosure are inhibitors of cell death. In any event, the compounds of the present disclosure preferably exert their effect on inhibiting cell death at a concentration less than about 50 micromolar, or at a concentration less than about 10 micromolar, or at a concentration less than 1 micromolar.

In certain embodiments, the present disclosure relates to a pharmaceutical composition comprising compound 7, or a pharmaceutically acceptable salt, isotopically enriched analog, tautomer, or prodrug thereof. In certain embodiments, the present disclosure relates to a pharmaceutical composition comprising compound 7, or a pharmaceutically acceptable salt, isotopically enriched analog, tautomer, or prodrug thereof, for inhibiting LRRK2 kinase. In certain embodiments, the present disclosure relates to a pharmaceutical composition comprising compound 7, or a pharmaceutically acceptable salt, isotopically enriched analog, tautomer, or prodrug thereof, for treating Crohn's disease. In other embodiments, provided is a pharmaceutical composition comprising compound 7, or a pharmaceutically acceptable salt, isotopically enriched analog, tautomer, or prodrug thereof, for treating Parkinson's disease.

In certain embodiments, the present disclosure relates to a compound, or a pharmaceutically acceptable salt, isotopically enriched analog, tautomer, stereoisomer, mixture of stereoisomers, or prodrug thereof, for inhibiting LRRK2 kinase, wherein the compound is as described herein (e.g., Table 1 or Table 2). In certain embodiments, the LRRK2 kinase is G2019S or N2081D. In certain embodiments, the compound inhibits LRRK2 kinase, e.g., G2019S, at an $IC_{50}$ concentration of less than about 5 micromolar, or less than 1 micromolar. In certain embodiments, the compound inhibits LRRK2 kinase, e.g., G2019S, at an $IC_{50}$ concentration of less than about 3 nanomolar. In certain embodiments, the compound inhibits LRRK2 kinase according to the cellular assay of Biological Example 4 at an $IC_{50}$ concentration of less than about 11, 5, 4, 3 or 2 nanomolar.

4. Kits

Provided herein are also kits that include a compound of the disclosure, or a pharmaceutically acceptable salt, isotopically enriched analog, tautomer, stereoisomer, mixture of stereoisomers, or prodrug thereof, and suitable packaging. In certain embodiments, a kit further includes instructions for use. In one aspect, a kit includes a compound of the disclosure, or a pharmaceutically acceptable salt, isotopically enriched analog, tautomer, stereoisomer, mixture of stereoisomers, or prodrug thereof, and a label and/or instructions for use of the compounds in the treatment of the indications, including the diseases or conditions, described herein.

Provided herein are also articles of manufacture that include a compound described herein or a pharmaceutically acceptable salt, or a pharmaceutically acceptable salt, isotopically enriched analog, tautomer, stereoisomer, mixture of stereoisomers, or prodrug thereof in a suitable container. The container may be a vial, jar, ampoule, preloaded syringe, or intravenous bag.

5. Pharmaceutical Compositions and Modes of Administration

Compounds provided herein, or a pharmaceutically acceptable salt, isotopically enriched analog, tautomer, stereoisomer, mixture of stereoisomers, or prodrug thereof, are usually administered in the form of pharmaceutical compositions. Thus, provided herein are also pharmaceutical compositions that contain one or more of the compounds described herein or a pharmaceutically acceptable salt, isotopically enriched analog, tautomer, stereoisomer, mixture of stereoisomers, or prodrug thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). In some embodiments, the pharmaceutical composition is in a solid, oral dosage form.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein, or a pharmaceutically acceptable salt, isotopically enriched analog, tautomer, stereoisomer, mixture of stereoisomers, or prodrug thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein, or a pharmaceutically acceptable salt, isotopically enriched analog, tautomer, stereoisomer, mixture of stereoisomers, or prodrug thereof, thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Transdermal patches may be used to provide continuous or discontinuous infusion of the compounds described herein in controlled amounts. Transdermal patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, isotopically enriched analog, tautomer, stereoisomer, mixture of stereoisomers, or prodrug thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In certain embodiments, the compositions are administered by the oral or nasal respiratory route for local or systemic effect. In certain embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

6. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In certain embodiments, about 0.1 and 100 mg/kg may be appropriate.

In certain embodiments a dosage of between 0.5 and 60 mg/kg may be appropriate. In certain embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound as described herein (e.g., Table 1 or Table 2) may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, four, or more times daily, using any suitable mode described above.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

7. Combination Therapy

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; hypertension, hypercholesterolemia and type II diabetes; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

In certain embodiments, a compound, or a pharmaceutically acceptable salt, isotopically enriched analog, tautomer, stereoisomer, mixture of stereoisomers, or prodrug thereof, of the present disclosure can be administered in combination with an additional agent having activity for treatment of a neurodegenerative disease. For example, in some embodiments the compounds are administered in combination with one or more additional therapeutic agents useful for treatment of Parkinson's disease. In certain embodiments, the additional therapeutic agent is L-dopa (e.g., Sinemet®), a dopaminergic agonist (e.g. Ropinerol or Pramipexole), a catechol-O-methyltransferase (COMT) inhibitor (e.g. Entacapone), a L-monoamine oxidase (MAO) inhibitor (e.g., selegiline or rasagiline) or an agent which increases dopamine release (e.g., Zonisamide).

In some embodiments the compounds are administered in combination with one or more additional therapeutic agents useful for treatment of Crohn's disease. In certain embodiments, the additional therapeutic agent is a corticosteroid (e.g. prednisone and budesonide), a 5-aminosalicylate (e.g. sulfasalazine, sulfa, and mesalamine), an immune system suppressor (e.g. azathioprine, mercaptopurine, Infliximab, adalimumab, certolizumab pegol, methotrexate, natalizumab, vedolizumab, and ustekinumab), and antibiotics (e.g. ciprofloxacin and metronidazole).

The present disclosure also provides a combination of two or more compounds, or a pharmaceutically acceptable salt, isotopically enriched analog, tautomer, stereoisomer, mixture of stereoisomers, or prodrug thereof, that inhibit cellular necrosis (e.g., a compound as disclosed herein and an additional agent for inhibiting necrosis). The present disclosure also provides combinations of one or more compounds that inhibit cellular necrosis combined with one or more additional agents or compounds (e.g., other therapeutic compounds for treating a disease, condition, or infection).

8. Synthesis of the Compounds

The compounds, or pharmaceutically acceptable salts, deuterated analogs, tautomers, stereoisomers, mixture of stereoisomers, or prodrug thereof may be prepared using the methods disclosed herein and routine modifications thereof, which will be apparent given the disclosure herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art.

Additionally, as will be apparent to those skilled in the art, protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin., USA), Bachem (Torrance, California., USA), Emka-Chemce or Sigma (St. Louis, Missouri., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

General Synthesis

The following General Reaction Scheme I illustrates a general method of making a compound disclosed herein.

Scheme I

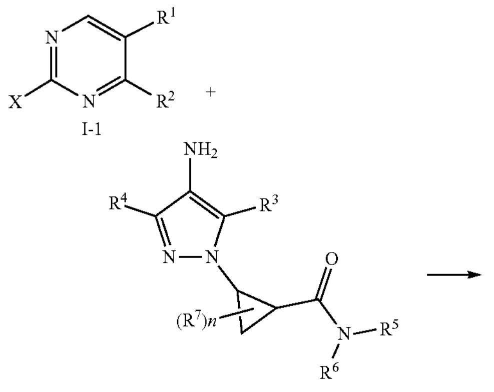

I-1

I-2

-continued

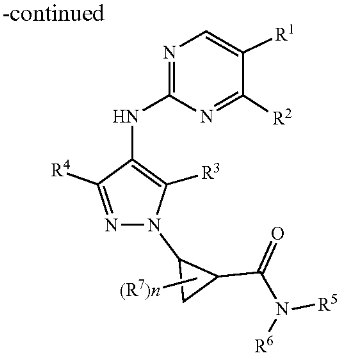

I

Referring to General Reaction Scheme I, compounds of Formula I can be prepared by coupling a substituted pyrimidine of Formula I-1 with an amine of Formula I-2, wherein $R^1$, $R^2$, $R^3$, $R^4$, $R^5$, $R^6$, $R^7$, and n are defined as in any of the formulas provided herein or by the specific compounds exemplified herein (e.g., Table 1 or Table 2), and X is a leaving group. In certain embodiments, X is halo. Appropriate compounds of Formula I-1 or I-2 can be prepared according to the more specific methods described as follows or by methods known to one of skill in the art. Coupling of compounds of Formula I-1 and I-2 in presence of an acid, provides a compound of Formula I. In certain embodiments, the acid is toluene sulfonic acid or trifluoracetic acid. In certain embodiments, coupling of compounds of Formula I-1 and I-2 in the presence of a base provides a compound of Formula I. In certain embodiments, the base is triethylamine.

In certain embodiments, provided is a method of preparing a compound of Formula I comprising coupling a compound of Formula I-1 with a compound of Formula I-2 under conditions to provide the compound of Formula I, wherein $R^1$, $R^2$, $R^3$, $R^4$, $R^5$, $R^6$, $R^7$, and n are defined as in any of the formulas provided herein or by the specific compounds exemplified herein (e.g., Table 1 or Table 2), and X is a leaving group. In certain embodiments, X is halo.

When not commercially available, amines of Formula I-2 can be prepared from commercially available starting materials. For example, in certain embodiments, amines of Formula I-2 can be prepared from reducing the corresponding nitro substituted compound. The amines of Formula I-2 are typically functionalized prior to the coupling with the substituted pyrimidine of Formula I-1. Where a certain stereoisomer of Formula I is desired, a single stereoisomer of the corresponding amine may be prepared prior to coupling with the substituted pyrimidine of Formula I-1 and/or a resulting mixture of stereoisomers can be resolved using known methods (e.g., chiral chromatography).

Exemplary amines of Formula I-2 can be prepared via 1,3-dipolar cycloaddition reactions using appropriately functionalized starting materials as shown in Scheme II.

Scheme II

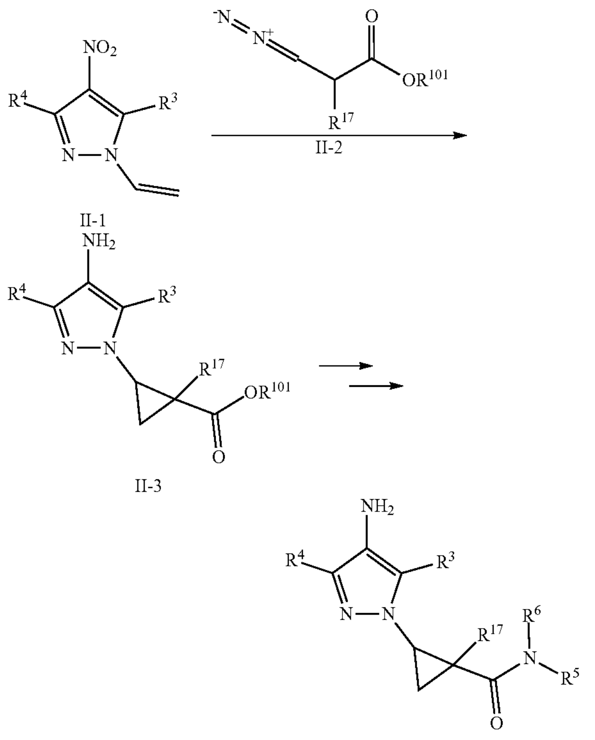

As shown above in Scheme II, a substituent can be installed during formation of the cyclopropyl ring by using an appropriately substituted starting material, where $R^3$, $R^4$, $R^5$, $R^6$ and $R^{17}$ are as defined herein, and $R^{101}$ is alkyl. In certain embodiments, $R^{101}$ is methyl. Appropriately substituted pyrazoles of Formula II-1 can be coupled with appropriately substituted diazo compounds of Formula II-2 in the presence of a catalyst to provide cyclopropyl intermediates of Formula II-3. Further functionalization/functional group interconversion may be performed using methods known in the art to provide amines of Formula II-4 for use in the method of Scheme I.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Experimental Methods:

All non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform (67.26), methanol (63.31), or DMSO (62.50) for $^1$H NMR. HPLC analysis was performed on Shimadzu 20AB HPLC system with a photodiode array detector and Luna-C18(2) 2.0×50 mm, 5 μm column at a flow rate of 1.2 mL/min with a gradient solvent Mobile phase A (MPA, $H_2O$+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HCl/$H_2O$=0.04%, or formic acid/$H_2O$=0.2% (v/v); MPB: ACN. Neutral: Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 um column at a flow rate of 4 mL/min with a gradient solvent Mobile phase A (MPA, $CO_2$): Mobile phase B (MPB, MeOH+0.05% (v/v) IPAm) (0.01 min, 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, 5 μm column at a flow rate of 65 mL/min with a gradient solvent Mobile phase A (MPA, $CO_2$): Mobile phase B (MPB, MeOH+0.1% (v/v) $NH_3H_2O$) (0.01 min, 10% MPB; 5 min, 40% MPB; 6 min, 40% MPB; 6.1-10 min, 10% MPB).

Compound Preparation

Where the preparation of starting materials is not described, these are commercially available, known in the literature or readily obtainable by those skilled in the art using standard procedures. known in the literature or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Example 1

Synthesis of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarboxamide (1)

A racemic mixture of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarbonitrile was separated by chiral SFC (column: IC (250 mm*30 mm, 10 μm); mobile phase: [Neu-IPA]; B %: 20%-20%, 3 min). To a solution of the second eluting isomer of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarbonitrile (41.3 mg, 0.11 mmol) in DMSO (2 mL), and sat. aq. $K_2CO_3$ (0.7 mL) was added UHP (119 mg, 1.27 mmol) at 25° C. under $N_2$. The mixture was stirred at 25° C. for 6 h. The mixture was poured into water (20 mL) at 20° C., extracted with EtOAc (3×10 mL). The combined organic layers were washed with brine (3×10 mL), dried over $Na_2SO_4$, filtered and concentrated under reduced pressure. The residue was purified by prep-HPLC under the following conditions: column: Waters Xbridge 150*25 5 μm; mobile phase: [water (10 mM $NH_4HCO_3$)-ACN]; B %: 20%-45%, 7 min to give the desired product. LC-MS, m/z=410.1 $[M+H]^+$. $^1H$ NMR (400 MHz, MeOD): δ 8.24 (br s, 1H), 8.03 (s, 1H), 3.64 (dd, J=5.3, 7.9 Hz, 1H), 2.24-2.17 (m, 4H), 1.49 (s, 3H), 1.47 (s, 3H), 1.30 (dd, J=5.9, 7.7 Hz, 1H), 0.86 (br s, 2H), 0.78 (br s, 2H).

Example 2

Synthesis of (1,2-cis)-2-(3-cyclopropyl-4-((4-(methylamino)-5-(trifluoromethyl)pyrimidin-2-yl)amino)-1H-pyrazol-1-yl)cyclopropanecarboxamide (2)

A racemic mixture of (1,2-cis)-2-(3-cyclopropyl-4-((4-(methylamino)-5-(trifluoromethyl)pyrimidin-2-yl)amino)-1H-pyrazol-1-yl)cyclopropanecarbonitrile was separated by chiral SFC (Instrument: Thar SFC80 preparative SFC; Column: Chiralpak AD-H 250*30 mm i.d. 5 μm; Mobile phase: A for $CO_2$ and B for EtOH (0.1% $NH_3H_2O$); Gradient: B %=42%; Flow rate: 70 g/min; Wavelength: 220 nm; Column temperature: 40° C.; System back pressure: 100 bar). To a solution of the first eluting isomer of (1,2-cis)-2-(3-cyclopropyl-4-((4-(methylamino)-5-(trifluoromethyl)pyrimidin-2-yl)amino)-1H-pyrazol-1-yl)cyclopropanecarbonitrile (51 mg, 0.14 mmol) in DMSO (3 mL) was added sat. aq. $K_2CO_3$ (0.9 mL) and UHP (160 mg, 1.70 mmol) at 25° C. under $N_2$. The mixture was stirred at 25° C. for 12 h. The mixture was poured into water (20 mL) at 20° C., extracted with EtOAc (3×10 mL). The combined organic layers were washed with brine (30 mL), dried over $Na_2SO_4$, filtered and concentrated under reduced pressure. The residue was purified by prep-HPLC under the following conditions: column: Waters Xbridge 150*25 5 μm; mobile phase: [water (10 mM $NH_4HCO_3$)-ACN]; B %: 10%-40%, 7 min to provide the desired product. LC-MS, m/z=382.1 $[M+H]^+$. $^1H$ NMR (400 MHz, MeOD): δ 8.02 (s, 1H), 7.96 (br s, 1H), 3.87-3.77 (m, 1H), 3.02 (s, 3H), 2.19-2.07 (m, 1H), 1.95 (q, J=5.7 Hz, 1H), 1.87-1.74 (m, 1H), 1.46 (dt, J=5.9, 8.0 Hz, 1H), 0.93-0.74 (m, 4H).

Example 3

Synthesis of (1,2-cis)-2-(4-((5-bromo-4-(ethylamino)pyrimidin-2-yl)amino)-3-methyl-1H-pyrazol-1-yl)-1-methylcyclopropanecarboxamide (3)

A racemic mixture of (1,2-cis)-2-(4-((5-bromo-4-(ethylamino)pyrimidin-2-yl)amino)-3-methyl-1H-pyrazol-1-yl)-1-methylcyclopropanecarbonitrile was separated by chiral SCF (column: IC (250 mm*30 mm, 10 um); mobile phase: [Neu-IPA]; B %: 33%-33%, 5 min). To a solution of the first eluting isomer of (1,2-cis)-2-(4-((5-bromo-4-(ethylamino)pyrimidin-2-yl)amino)-3-methyl-1H-pyrazol-1-yl)-1-methylcyclopropanecarbonitrile (60.70 mg, 0.16 mmol) in DMSO (3 mL) was added sat. aq. $K_2CO_3$ (0.9 mL) and UHP (182 mg, 1.94 mmol) at 25° C. under $N_2$. The mixture was stirred at 25° C. for 12 h. The reaction mixture was poured into water (10 mL) at 20° C., extracted with EtOAc (3×5 mL). The combined organic layers were washed with brine (3×5 mL), dried over $Na_2SO_4$, filtered and concentrated under reduced pressure. The residue was purified by prep-HPLC under the following conditions: column: Waters Xbridge 150*25 5 μm; mobile phase: [water (10 mM $NH_4HCO_3$)-ACN]; B %: 10%-40%, 7 min to give the desired product. LC-MS, m/z=394.0, 396.0 $[M+H]^+$. $^1H$ NMR (400 MHz, MeOD): δ 7.83-7.78 (m, 2H), 3.62 (dd, J=5.3, 7.9 Hz, 1H), 3.50 (q, J=7.2 Hz, 2H), 2.20 (t, J=5.5 Hz, 1H), 2.15 (s, 3H), 1.47 (s, 3H), 1.29 (dd, J=5.7, 7.9 Hz, 1H), 1.24 (t, J=7.2 Hz, 3H).

Example 4

Synthesis of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarboxamide (4)

A racemic mixture of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarbonitrile was separated by chiral SFC (column: IC (250 mm*30 mm, 10 μm); mobile phase: [Neu-IPA]; B %: 20%-20%, 3 min). To a solution of the first eluting isomer of (1,2-cis)-1-methyl-2-(3-methyl-4-((4-((1-methylcyclopropyl)amino)-5-(trifluoromethyl)pyrimidin-2-yl)amino)-1H-pyrazol-1-yl)cyclopropanecarbonitrile (20 mg, 0.05 mmol) in DMSO (1 mL) and sat. aq. $K_2CO_3$ (3 mL) was added UHP (58 mg, 0.61 mmol) at 25° C. under $N_2$. The mixture was stirred at 25° C. for 15 h. The mixture was poured into water (10 mL). The aqueous phase was extracted with EtOAc (4×3 mL). The combined organic phase was washed with brine (3 mL), dried over anhydrous $Na_2SO_4$, filtered and concentrated under reduced pressure. The residue was purified by prep-HPLC (neutral) under the following conditions: column: Xtimate C18 150*25 mm*5 μm; mobile phase: [water (10 mM $NH_4HCO_3$)-ACN]; B %: 25%-55%, 10 min to provide the desired product. LC-MS: m/z: 409.9 [M+H]+. $^1H$-NMR (400 MHz, $CDCl_3$): δ 8.27 (br s, 1H), 8.10 (br s, 1H), 6.77 (br s, 1H), 5.76 (br s, 1H), 5.53 (br s, 1H), 5.20 (br s, 1H), 3.66 (dd, J=5.2, 8.0 Hz, 1H), 2.24 (s, 3H), 2.19 (t, J=5.6 Hz, 1H), 1.57-1.51 (m, 1H), 1.53 (s, 2H), 1.49 (s, 3H), 1.31 (dd, J=6.2, 7.9 Hz, 1H), 0.97-0.74 (m, 4H).

Example 5

Synthesis of (1R,2S)- and (1S,2R)-2-(3-cyclopropyl-4-((4-(ethylamino)-5-(trifluoromethyl)pyrimidin-2-yl)amino)-1H-pyrazol-1-yl)-1-methylcyclopropanecarbonitrile (5)

Methyl 2,2-dibromo-1-methyl-cyclopropanecarboxylate: To a mixture of methyl 2-methylprop-2-enoate (110.28 g, 1.10 mol), benzyl(triethyl)ammonium chloride (30.01 g, 131.75 mmol) and NaOH (449.88 g, 11.25 mol) in $H_2O$ (443.5 mL), bromoform (557.44 g, 2.21 mol) was added dropwise at 0° C. Then the mixture was stirred at 25° C. for 12 h. The reaction mixture was filtered and then diluted with water (500 mL) and extracted with MTBE (3×500 mL). The combined organic layer was washed with brine (2×300 mL), dried over $Na_2SO_4$, filtered and concentrated under reduced pressure. The residue was purified by silica gel column chromatography (PE:EtOAc=30:1 to 1:1) to give methyl 2,2-dibromo-1-methyl-cyclopropanecarboxylate. $^1H$ NMR (400 MHz, $CDCl_3$): δ ppm 3.80 (s, 3H), 2.43 (d, J=7.94 Hz, 2H), 1.59 (d, J=7.94 Hz, 3H).

Cis and trans-methyl 2-bromo-1-methyl-cyclopropanecarboxylate: To a solution of methyl 2,2-dibromo-1-methyl-cyclopropanecarboxylate (114 g, 419.22 mmol) in THF (500 mL), i-PrMgCl (230.57 mL, 2 M) was added dropwise at −78° C. under $N_2$. The mixture was stirred for 5 min. The reaction mixture was quenched by sat. $NH_4Cl$ (100 mL) at 20° C., and then diluted with water (200 mL). The organic phase was separated and the aqueous phase was extracted with EtOAc (2×500 mL). The combined organic phase was washed with brine (500 mL), dried over $Na_2SO_4$, filtered and concentrated under reduced pressure to give a mixture of cis and trans methyl 2-bromo-1-methyl-cyclopropanecarboxylate. The crude product was used for the next step without further purification. $^1$H NMR (400 MHz, $CDCl_3$): δ ppm 3.77 (s, 3H), 3.69 (s, 3H), 3.52 (dd, J=8.16, 5.29 Hz, 1H), 2.96 (dd, J=7.72, 5.51 Hz, 1H), 1.79-1.88 (m, 2H), 1.40 (s, 3H), 1.48 (s, 3H), 1.23-1.27 (m, 1H), 1.02 (t, J=5.62 Hz, 1H).

Cis and trans-2-bromo-1-methyl-cyclopropanecarboxylic acid: A solution of methyl 2-bromo-1-methyl-cyclopropanecarboxylate (71 g, 367.80 mmol) in MeOH (500 mL) and $H_2O$ (50 mL) was added NaOH (44.12 g, 1.10 mol). The mixture was stirred at 25° C. for 16 h. The mixture was concentrated under reduced pressure. The residue was diluted with water (500 mL). The aqueous phase was extracted with MTBE (300 mL) to remove the impurity, then the aqueous phase was adjusted to pH=3 by aq. HCl (2M) and extracted with DCM (400 mL×2). The combined organic phase was washed with brine (300 mL), dried over $Na_2SO_4$, filtered and concentrated under reduced pressure to give a mixture of cis and trans 2-bromo-1-methyl-cyclopropanecarboxylic acid. The crude product was used for the next step without further purification. $^1$H NMR (400 MHz, $CDCl_3$): δ ppm 3.58 (dd, J=8.53, 5.52 Hz, 1H), 3.02 (dd, J=7.78, 5.77 Hz, 1H), 1.92 (dd, J=8.03, 6.02 Hz, 1H), 1.81 (t, J=6.02 Hz, 1H), 1.41 (s, 3H), 1.32 (dd, J=7.53, 6.53 Hz, 1H), 1.21 (s, 3H), 1.09 (t, J=5.77 Hz, 1H).

Cis and trans-2-Bromo-N-tert-butyl-1-methyl-cyclopropanecarboxamide: A solution of 2-bromo-1-methyl-cyclopropanecarboxylic acid (60 g, 335.17 mmol) in $SOCl_2$ (370 mL) was heated to 80° C. and stirred for 2 h. Then the mixture was concentrated under reduced pressure. The residue was dissolved in THF (200 mL). The solution was added dropwise to a mixture of TEA (74.22 g, 733.46 mmol) and 2-methylpropan-2-amine (30.09 g, 411.42 mmol) in THF (500 mL) at 0° C. under $N_2$. The mixture was warmed to 25° C. and stirred for 1 h. The mixture was quenched by HCl (500 mL, 2M) and then adjusted to pH=7 by sat. $NaHCO_3$. The organic phase was separated and the aqueous phase was extracted with EtOAc (500 mL×2). The combined organic phase was washed with brine (500 mL), dried over $Na_2SO_4$, filtered and concentrated under reduced pressure to give cis and trans-2-bromo-N-tert-butyl-1-methyl-cyclopropanecarboxamide. LCMS: RT 1.365 min, m/z=235.1 $[M+H]^+$. $^1$H NMR (400 MHz, $CDCl_3$): δ ppm 5.43-5.68 (m, 1H), 3.47 (dd, J=8.03, 5.02 Hz, 1H), 2.86 (dd, J=7.53, 4.52 Hz, 1H), 1.83 (dd, J=8.03, 6.02 Hz, 1H), 1.63 (dd, J=6.78, 4.77 Hz, 1H), 1.47 (s, 3H), 1.34-1.40 (m, 12H), 1.11-1.16 (m, 1H), 0.83-0.87 (m, 1H).

N-tert-butyl-1-methyl-cycloprop-2-ene-1-carboxamide: To a mixture of 2-bromo-N-tert-butyl-1-methyl-cyclopropanecarboxamide (5.5 g, 23.49 mmol) in DMSO (15 mL) was added KOH (2.64 g, 46.98 mmol) and 18-crown-6 (621 mg, 2.35 mmol) at 25° C. The mixture was stirred at 25° C. for 72 h. The reaction mixture was diluted with water (50 mL) and extracted with DCM:i-PrOH (3×50 mL, v:v=3:1). Then the combined organic layer was washed with brine (3×10 mL), dried over $Na_2SO_4$, filtered and concentrated under reduced pressure. The residue was purified by silica gel column chromatography (PE:EtOAc=20:1 to 5:1) to give N-tert-butyl-1-methyl-cycloprop-2-ene-1-carboxamide. LCMS: RT 1.027 min, m/z=154.2 $[M+H]^+$. $^1$H NMR (400 MHz, $CDCl_3$): δ ppm 7.09 (s, 2H), 1.36 (s, 3H), 1.29 (s, 9H).

(1,2-cis)-N-(tert-butyl)-2-(3-cyclopropyl-1H-pyrazol-1-yl)-1-methylcyclopropanecarboxamide: To a mixture of 3-cyclopropyl-1H-pyrazole (2.82 g, 26.11 mmol) in THF (30 mL) was added 18-crown-6 (690 mg, 2.61 mmol) and NaH (2.09 g, 52.21 mmol, 60% purity). The mixture was stirred at 25° C. for 0.5 h. N-tert-butyl-1-methyl-cycloprop-2-ene-1-carboxamide (4 g, 26.11 mmol) was added to the reaction solution. The mixture was then stirred at 80° C. for another 16 h. The reaction mixture was diluted with water (100 mL) and extracted with MTBE (3×100 mL). The combined organic layer was washed with brine (2×20 mL), dried over $Na_2SO_4$, filtered and concentrated under reduced pressure. The residue was purified by silica gel column chromatography (PE:EtOAc=10:1 to 1:1) and prep-HPLC (TFA) to give (1,2-cis)-N-(tert-butyl)-2-(3-cyclopropyl-1H-pyrazol-1-yl)-1-methylcyclopropanecarboxamide. LCMS: RT 1.248 min, m/z=262.18 $[M+H]^+$. $^1$H NMR (400 MHz, $CDCl_3$): δ ppm 7.26 (d, J=2.4 Hz, 1H), 5.80 (d, J=2.4 Hz, 1H), 5.72 (br.s, 1H), 3.56 (dd, J=5.1, 7.9 Hz, 1H), 2.02 (dd, J=5.1, 6.4 Hz, 1H), 1.95-1.88 (m, 1H), 1.43 (s, 3H), 1.13 (s, 9H), 0.90 (dd, J=2.2, 8.6 Hz, 2H), 0.75-0.60 (m, 3H).

(1,2-cis)-N-(tert-butyl)-2-(3-cyclopropyl-4-nitro-1H-pyrazol-1-yl)-1-methylcyclopropanecarboxamide: To a mixture of $Cu(NO_3)_2.3H_2O$ (18.03 g, 74.61 mmol) in $Ac_2O$ (30 mL) was added (1,2-cis)-N-tert-butyl-2-(3-cyclopropylpyrazol-1-yl)-1-methyl-cyclopropanecarboxamide (1.95 g, 7.46 mmol). The mixture was stirred at 25° C. for 16 h. The reaction mixture was diluted with $H_2O$ (100 mL) and extracted with EtOAc (3×100 mL). The combined organic layer was washed with brine (3×20 mL), dried over $Na_2SO_4$, filtered and concentrated under reduced pressure to give (1,2-cis)-N-(tert-butyl)-2-(3-cyclopropyl-4-nitro-1H-pyrazol-1-yl)-1-methylcyclopropanecarboxamide. The crude was used into next step without purification. LCMS: RT 1.245 min, m/z=307.2 $[M+H]^+$. $^1$H NMR (400 MHz, $CDCl_3$): δ ppm 8.08 (s, 1H), 5.60 (br s, 1H), 3.68-3.40 (m, 1H), 2.61-2.51 (m, 1H), 2.25-2.22 (m, 1H), 1.46 (s, 3H), 1.19 (s, 9H), 1.07-0.91 (m, 4H).

(1,2-cis)-2-(3-cyclopropyl-4-nitro-1H-pyrazol-1-yl)-1-methylcyclopropanecarbonitrile: (1,2-cis)-N-tert-butyl-2-(3-cyclopropyl-4-nitro-pyrazol-1-yl)-1-methyl-cyclopropanecarboxamide (2.2 g, 7.18 mmol) in T3P (30 mL, 50% in EtOAc) was stirred at 80° C. for 4 h. The reaction mixture was diluted with $H_2O$ (50 mL) and extracted with EtOAc (3×50 mL). The combined organic layer was washed with brine (2×20 mL), dried over $Na_2SO_4$, filtered and concentrated under reduced pressure. The residue was purified by silica gel column chromatography (PE:EtOAc=20:1 to 5:1) to give (1,2-cis)-2-(3-cyclopropyl-4-nitro-1H-pyrazol-1-yl)-1-methylcyclopropanecarbonitrile. LCMS: RT 1.142 min, m/z=233.1 $[M+H]^+$. $^1$H NMR (400 MHz, $CDCl_3$): δ ppm 8.22 (s, 1H), 3.71 (dd, J=5.1, 7.7 Hz, 1H), 2.64-2.57 (m, 1H), 2.22 (dd, J=5.2, 7.0 Hz, 1H), 1.55 (s, 3H), 1.52 (s, 1H), 1.06-1.02 (m, 4H).

(1,2-cis)-2-(4-amino-3-cyclopropyl-1H-pyrazol-1-yl)-1-methylcyclopropanecarbonitrile: To a mixture of (1,2-cis)-2-(3-cyclopropyl-4-nitro-pyrazol-1-yl)-1-methyl-cyclopropanecarbonitrile (1 g, 4.31 mmol) in EtOH (10 mL) and $H_2O$ (1 mL) was added Fe (721 mg, 12.92 mmol) and $NH_4Cl$ (691 mg, 12.92 mmol). The mixture was stirred at 80° C. for 4 h. The reaction mixture was filtered through a pad of celite, the filtrate was concentrated under reduced pressure. The residue was extracted with EtOAc (3×50 mL). The combined organic layer was washed with brine (2×10 mL), dried over $Na_2SO_4$, filtered and concentrated under reduced pressure to give (1,2-cis)-2-(4-amino-3-cyclopropyl-1H-pyrazol-1-yl)-1-methylcyclopropanecarbonitrile, which was used into the next step without further purification. LCMS: RT 0.779 min, m/z=203.1 $[M+H]^+$. $^1H$ NMR (400 MHz, $CDCl_3$): δ ppm 7.02 (s, 2H), 3.57 (dd, J=5.3, 7.5 Hz, 1H), 2.13 (br t, J=5.8 Hz, 1H), 1.74-1.63 (m, 1H), 1.48 (s, 3H), 1.37 (br t, J=7.2 Hz, 1H), 0.89-0.80 (m, 4H).

(1R,2S)- and (1S,2R)-2-(3-cyclopropyl-4-((4-(ethylamino)-5-(trifluoromethyl)pyrimidin-2-yl)amino)-1H-pyrazol-1-yl)-1-methylcyclopropanecarbonitrile: To the mixture of (1,2-cis)-2-(4-amino-3-cyclopropyl-pyrazol-1-yl)-1-methyl-cyclopropanecarbonitrile (650 mg, 3.21 mmol) and 2-chloro-N-ethyl-5-(trifluoromethyl)pyrimidin-4-amine (653 mg, 2.89 mmol) in 1,4-dioxane (40 mL) was added p-TsOH·$H_2O$ (611 mg, 3.21 mmol) at 25° C. The mixture solution was stirred at 90° C. for 4 h. The reaction mixture was diluted with $H_2O$ (50 mL), adjusted to pH=7 by sat. $NaHCO_3$, then extracted with EtOAc (2×50 mL). The combined organic layer was washed with brine (2×10 mL), dried over $Na_2SO_4$, filtered and concentrated under reduced pressure. The residue was purified by silica gel column chromatography (PE:EtOAc=20:1 to 5:1) to give (1,2-cis)-2-(3-cyclopropyl-4-((4-(ethylamino)-5-(trifluoromethyl)pyrimidin-2-yl)amino)-1H-pyrazol-1-yl)-1-methylcyclopropanecarbonitrile as a racemate. The product was further separated by chiral SFC (column: AD (250 mm*30 mm, 5 μm); mobile phase: [0.1% $NH_3H_2O$ MEOH]; B %: 30%-30%, 5.5 min) to give (1R,2S)- and (1S,2R)-2-(3-cyclopropyl-4-((4-(ethylamino)-5-(trifluoromethyl)pyrimidin-2-yl)amino)-1H-pyrazol-1-yl)-1-methylcyclopropanecarbonitrile.

First eluting isomer by SFC: To product obtained from SFC was added MTBE (3 mL) and the mixture was heated to 60° C. until dissolved. The solution was filtered. n-Heptane (20 mL) was added to the stirring filtrate until it turned cloudy. The mixture was then stirred at 25° C. for 12 h. The precipitated product was collected by filtration and dried under reduced pressure. LCMS: RT 1.083 min, m/z=392.2 $[M+H]^+$. $^1H$ NMR (400 MHz, $CDCl_3$): δ ppm 8.15 (br s, 1H), 8.00 (s, 1H), 7.07-6.82 (m, 1H), 5.15 (br d, J=16.1 Hz, 1H), 3.68 (dd, J=5.2, 7.7 Hz, 1H), 3.59 (br s, 2H), 2.17 (br s, 1H), 1.77-1.68 (m, 1H), 1.52 (s, 3H), 1.44 (br t, J=7.2 Hz, 1H), 1.32 (br s, 3H), 0.96-0.90 (m, 2H), 0.90-0.84 (m, 2H).

Second eluting isomer by SFC: To product obtained from SFC was added MTBE (3 mL) and the mixture was heated to 60° C. until dissolved. The solution was filtered. n-Heptane (20 mL) was added to the stirring filtrate until it turned cloudy. The mixture was then stirred at 25° C. for 12 h. The precipitated product was collected by filtration and dried under reduced pressure. LCMS: RT 1.084 min, m/z=392.2 $[M+H]^+$. $^1H$ NMR (400 MHz, $CDCl_3$): δ ppm 8.15 (br s, 1H), 8.01 (s, 1H), 7.15-6.62 (m, 1H), 5.41-4.80 (m, 1H), 3.68 (dd, J=5.1, 7.7 Hz, 1H), 3.59 (br s, 2H), 2.17 (br s, 1H), 1.77-1.68 (m, 1H), 1.59 (s, 3H), 1.44 (brt, J=7.1 Hz, 1H), 1.32 (br s, 3H), 0.97-0.90 (m, 2H), 0.90-0.83 (m, 2H).

(1,2-cis)-2-(3-cyclopropyl-4-((4-(ethylamino)-5-(trifluoromethyl)pyrimidin-2-yl)amino)-1H-pyrazol-1-yl)-1-methylcyclopropanecarboxamide: To a solution of the SFC first eluting enantiomer of (1,2-cis)-2-(3-cyclopropyl-4-((4-(ethylamino)-5-(trifluoromethyl)pyrimidin-2-yl)amino)-1H-pyrazol-1-yl)-1-methylcyclopropanecarbonitrile (150 mg, 0.38 mmol) in DMSO (5 mL) was added sat. aq. $K_2CO_3$ (0.3 mL) and UHP (432 mg, 4.59 mmol) at 25° C. under $N_2$. The mixture was stirred at 25° C. for 12 h. The mixture was poured into water (20 mL) at 20° C., extracted with EtOAc (3×10 mL). The combined organic layers were washed with brine (3×10 mL), dried over $Na_2SO_4$, filtered and concentrated under reduced pressure. The residue was purified by prep-HPLC under the following conditions: column: Xtimate C18 150*40 mm*10 μm; mobile phase: [water (10 mM $NHHCO_3$)-ACN]; B %: 35%-65%, 7 min to provide the desired product. LC-MS, m/z=410.1 $[M+H]^+$. $^1H$ NMR (400 MHz, $CDCl_3$): δ 8.12 (br s, 1H), 7.91 (s, 1H), 6.98 (br d, J=18.1 Hz, 1H), 5.81 (br s, 1H), 5.35-5.02 (m, 2H), 3.63 (dd, J=5.1, 7.9 Hz, 1H), 3.60-3.52 (m, 2H), 2.13 (brt, J=5.6 Hz, 1H), 1.75-1.66 (m, 1H), 1.46 (s, 3H), 1.35-1.27 (m, 3H), 1.26 (s, 1H), 0.90 (dd, J=1.8, 8.3 Hz, 2H), 0.85-0.73 (m, 2H).

Example 6

Synthesis of (1,2-cis)-2-(4-((4-(cyclopropylamino)-5-(trifluoromethyl)pyrimidin-2-yl)amino)-3-methyl-1H-pyrazol-1-yl)-1-methylcyclopropanecarboxamide (6)

A racemic mixture of (1,2-cis)-2-(4-((4-(cyclopropylamino)-5-(trifluoromethyl)pyrimidin-2-yl)amino)-3-methyl-1H-pyrazol-1-yl)-1-methylcyclopropanecarbonitrile was separated by chiral SCF (column: AD (250 mm*30 mm, 5 μm); mobile phase: [0.1% $NH_3H_2O$ MEOH]; B %: 40%-40%, 5 min). To a solution of the first eluting isomer of (1,2-cis)-2-(4-((4-(cyclopropylamino)-5-(trifluoromethyl)pyrimidin-2-yl)amino)-3-methyl-1H-pyrazol-1-yl)-1-methylcyclopropanecarbonitrile (19 mg, 0.05 mmol) in DMSO (1 mL) and sat. aq. $K_2CO_3$ (3 mL) was added UHP (57 mg, 0.6 mmol) at 25° C. under $N_2$. The mixture was stirred at 25° C. for 15 h. The mixture was poured into ice water (10 mL). The aqueous phase was extracted with EtOAc (4×3 mL). The combined organic phase was washed with brine (3 mL), dried over anhydrous $Na_2SO_4$, filtered and concentrated under reduced pressure. The residue was purified by prep-HPLC (neutral) under the following conditions: column: Xtimate C18 150*25 mm*5 μm; mobile phase: [water (10 mM $NH_4HCO_3$)-ACN]; B %: 20%-50%, 10 min to give the desired product. LC-MS: m/z: 395.9 $[M+H]^+$. $^1H$-NMR (400 MHz, $CDCl_3$): δ 8.23 (br s, 1H), 8.12 (br s, 1H), 6.91 (br s, 1H), 5.72 (br s, 1H), 5.41 (br s, 1H), 5.13 (br s, 1H), 3.66 (dd, J=5.2, 8.0 Hz, 1H), 2.92 (br s, 1H), 2.25 (s, 3H), 2.17 (br s, 1H), 1.48 (s, 3H), 1.31 (dd, J=6.4, 8.0 Hz, 1H), 0.93 (br s, 2H), 0.67 (br s, 2H).

Examples 7 and 8

Synthesis of (1,2-cis)-2-(3-cyclopropyl-4-((4-(ethylamino)-5-(trifluoromethyl)pyrimidin-2-yl)amino)-1H-pyrazol-1-yl)cyclopropanecarboxamide (7 and 8)

3-cyclopropyl-4-nitro-1-vinyl-pyrazole: To a mixture of 3-cyclopropyl-4-nitro-1H-pyrazole (7 g, 45.71 mmol) and BETAC (1.04 g, 4.57 mmol) in 1,2-dichloroethane (50 mL) was added NaOH (9.14 g, 228.55 mmol) and water (9 mL) at 20° C. under $N_2$. The mixture was stirred at 80° C. for 8 h. The reaction mixture was filtered and the filtrate was concentrated. The crude product was purified by silica gel column chromatography (PE:EtOAc=100:1 to 1:1) to give 3-cyclopropyl-4-nitro-1-vinyl-pyrazole. $^1H$ NMR (400 MHz, $CDCl_3$): δ ppm 8.23 (s, 1H), 6.87 (dd, J=15.55, 8.71 Hz, 1H), 5.70, (d, J=15.66 Hz, 1H), 5.06 (d, J=8.60 Hz, 1H), 2.53-2.68 (m, 1H), 0.97-1.11 (m, 4H).

(1,2-cis)-ethyl-2-(3-cyclopropyl-4-nitro-1H-pyrazol-1-yl)cyclopropanecarboxylate: To a solution of 3-cyclopropyl-4-nitro-1-vinyl-pyrazole (7.6 g, 42.42 mmol) in DCM (114 mL) was added 3-[3-(2-carboxy-2-methyl-propyl)phenyl]-2,2-dimethyl-propanoic acid; rhodium (II) acetate (0.32 g, 0.42 mmol) at 25° C. under $N_2$. A solution of ethyl 2-diazoacetate (29.04 g, 254.50 mmol) in DCM (61 mL) was then added dropwise at 25° C. over 10 h. After the addition, the mixture was stirred at 25° C. for 2 h. The mixture was concentrated under reduced pressure. The residue was purified by silica gel column chromatography (PE:EtOAc=10:1 to 1:1) to give (1,2-cis)-ethyl 2-(3-cyclopropyl-4-nitro-1H-pyrazol-1-yl)cyclopropanecarboxylate. $^1$H NMR (400 MHz, $CDCl_3$): δ 8.24-8.08 (m, 1H), 4.10-3.95 (m, 2H), 3.90 (dt, J=5.6, 7.5 Hz, 1H), 2.58 (tt, J=5.2, 8.1 Hz, 1H), 2.31-2.15 (m, 1H), 2.04-1.95 (m, 1H), 1.64-1.58 (m, 1H), 1.18 (t, J=7.2 Hz, 3H), 1.03-0.87 (m, 4H).

(1,2-cis)-2-(3-cyclopropyl-4-nitro-1H-pyrazol-1-yl)cyclopropanecarboxylic acid: To a solution of (1,2-cis)-ethyl 2-(3-cyclopropyl-4-nitro-1H-pyrazol-1-yl)cyclopropanecarboxylate (2.9 g, 10.93 mmol) in 1,4-dioxane (9 mL) was added HCl (2 M, 72.48 mL) at 25° C. under $N_2$. The mixture was heated to 60° C. and stirred for 15 h. The mixture was concentrated under reduced pressure to give (1,2-cis)-2-(3-cyclopropyl-4-nitro-1H-pyrazol-1-yl)cyclopropanecarboxylic acid. $^1$H NMR (400 MHz, $CDCl_3$): δ 8.15 (s, 1H), 4.12-3.92 (m, 2H), 2.64-2.51 (m, 1H), 2.29-2.18 (m, 1H), 2.05-1.94 (m, 1H), 1.60 (dt, J=6.4, 8.0 Hz, 1H), 1.08-0.79 (m, 4H).

(1,2-cis)-2-(3-cyclopropyl-4-nitro-1H-pyrazol-1-yl)cyclopropanecarboxamide: To a solution of (1,2-cis)-2-(3-cyclopropyl-4-nitro-1H-pyrazol-1-yl)cyclopropanecarboxylic acid (2.8 g, 11.8 mmol) in DMF (30 mL) was added $NH_4Cl$ (3.79 g, 70.82 mmol) and DIPEA (9.15 g, 70.82 mmol, 12.34 mL) at 25° C. under $N_2$. The mixture was stirred for 10 min, then HATU (8.98 g, 23.61 mmol) was added and the mixture was stirred for 2 h. The mixture was poured into water (150 mL). The aqueous phase was extracted with EtOAc (4×50 mL). The combined organic phase was washed with brine (50 mL), dried over anhydrous $Na_2SO_4$, filtered and concentrated under reduced pressure. The residue was purified by p-TLC (PE:EtOAc=100:1 to 0:1) to give (1,2-cis)-2-(3-cyclopropyl-4-nitro-1H-pyrazol-1-yl)cyclopropanecarboxamide.

(1,2-cis)-2-(4-amino-3-cyclopropyl-1H-pyrazol-1-yl)cyclopropanecarboxamide: To a solution of (1,2-cis)-2-(3-cyclopropyl-4-nitro-1H-pyrazol-1-yl)cyclopropanecarboxamide (0.8 g, 3.39 mmol) in EtOH (16 mL) and $H_2O$ (4 mL) was added $NH_4Cl$ (905.8 mg, 16.93 mmol) and Fe (945.6 mg, 16.93 mmol) at 25° C. The mixture was heated to 80° C. and stirred for 2 h. The mixture was filtered and concentrated under reduced pressure. The residue was washed with DCM:MeOH (10 mL, v:v=10:1) filter and filtrated was concentrated under reduced pressure to give (1,2-cis)-2-(4-amino-3-cyclopropyl-1H-pyrazol-1-yl)cyclopropanecarboxamide. $^1$H NMR (400 MHz, $CDCl_3$): δ 7.32 (s, 1H), 3.80-3.75 (m, 1H), 2.13-2.05 (m, 1H), 1.93-1.87 (m, 1H), 1.76 (tt, J=5.2, 8.3 Hz, 1H), 1.47-1.42 (m, 1H), 0.92-0.73 (m, 4H).

(1,2-cis)-2-(3-cyclopropyl-4-((4-(ethylamino)-5-(trifluoromethyl)pyrimidin-2-yl)amino)-1H-pyrazol-1-yl)cyclopropanecarboxamide: To a mixture of (1,2-cis)-2-(4-amino-3-cyclopropyl-1H-pyrazol-1-yl)cyclopropanecarboxamide (230 mg, 1.12 mmol) and 2-chloro-N-ethyl-5-(trifluoromethyl)pyrimidin-4-amine (251 mg, 1.12 mmol) in 1,4-dioxane (10 mL) was added p-TsOH (63 mg, 0.33 mmol) at 25° C. under N2. The mixture was heated to 90° C. and stirred for 2 h. The mixture was poured into water (10 mL) and adjusted to pH=7-8 with sat.$NaHCO_3$ and extracted with EtOAc (3×5 mL). The combined organic layers were washed with brine (5 mL), dried over $Na_2SO_4$, filtered and concentrated under reduced pressure. The mixture was purified by prep-HPLC under the following conditions: column: Waters Xbridge 150*25 5 μm; mobile phase: [water (10 mM $NH_4HCO_3$)-ACN]; B %: 20%-40%, 10 min to give the desired compound which was further separated by SFC (DAICEL CHIRALPAK AD-H (250 mm*30 mm, 5 μm); mobile phase: [0.1% $NH_3H_2O$ MEOH]; B %: 40%-40%, 8 min) to provide (1R,2S)- and (1S,2R)-2-(3-cyclopropyl-4-((4-(ethylamino)-5-(trifluoromethyl)pyrimidin-2-yl)amino)-1H-pyrazol-1-yl).

First eluting isomer by SFC (8): Retention Time: 3.450 min. LC-MS: m/z: 396.2 $[M+H]^+$. $^1$H-NMR (400 MHz, $CDCl_3$): δ 8.11 (br s, 1H), 7.93 (s, 1H), 6.43-7.04 (m, 1H), 5.79 (br s, 1H), 5.24 (br s, 2H), 3.88 (q, J=7.06 Hz, 1H), 3.60 (br s, 2H), 1.96-2.13 (m, 2H), 1.66-1.70 (m, 1H), 1.50 (td, J=7.77, 5.62 Hz, 1H), 1.32 (br s, 3H), 0.77-0.95 (m, 4H).

Second eluting isomer by SFC (7): Retention Time: 4.606 min. LC-MS: m/z: 396.2 $[M+H]^+$. SFC: Retention Time: 4.606 min. $^1$H-NMR (400 MHz, $CDCl_3$): δ 8.12 (br s, 1H), 7.95 (s, 1H), 6.43-7.01 (m, 1H), 5.73 (br s, 1H), 5.18 (br s, 2H), 3.82-3.99 (m, 1H), 3.60 (br s, 2H), 1.95-2.12 (m, 2H), 1.67-1.76 (m, 1H), 1.50 (td, J=8.05, 5.51 Hz, 1H), 1.32 (br s, 3H), 0.78-0.95 (m, 4H).

Biochemical Assays of the Compounds

Biological Example 1

Materials:
- LRRK2 G2019S enzyme
- Substrate (LRRKtide)
- ATP
- TR-FRET dilution buffer
- pLRRKtide antibody
- 384-well assay plate
- DMSO Enzyme Reaction Conditions
- 50 mM Tris pH 7.5, 10 mM $MgCl_2$, 1 mM EGTA, 0.01% Brij-35, 2 mM DTT
- 5 nM LRRK2
- 134 μM ATP
- 60 minute reaction time
- 23° C. reaction temperature
- 10 μL total reaction volume Detection Reaction Conditions
- 1×TR-FRET dilution buffer
- 10 mM EDTA
- 2 nM antibody
- 23° C. reaction temperature
- 10 μL total reaction volume Compounds are prepared by initially diluting to 1 mM with DMSO. 35 μL of reference compound solution, 35 μL of test compound solution, and 35 μL HPE are successively added to the source plate (384-well assay plate, Labcyte). The plates are centrifuged at 2500 rpm for 1 minute and sealed in foil. POD is used to perform a 3.162 fold serial dilution and 100 nL of reference compound solution, test compound solution, HPE and ZPE are transferred to assay plates. The assay plate is centrifuged at 2500 rpm for 1 minute, and sealed with foil.

To perform the enzyme reaction, 5 μL of LRRKtide substrate and kinase mixture in assay buffer is added to all wells of the assay plate. The plate is centrifuged to concentrate the mixture at the bottom of the wells. The assay plate is incubated at 23° C. for 20 minutes. Following incubation, 5 μL of 2×ATP in assay buffer is added to each well, and plates are centrifuged to concentrate the mixture at the bottom of the wells. The plate is incubated at 23° C. for 60 minutes.

To perform the detection of the reaction, EDTA completely mixed in TR-FRET dilution buffer is added to antibody reagent. 10 μL of detection reagent is added to all wells of each well of the assay plate and the plate is centrifuged to concentrate the mixture at the bottom of the wells. The plate is then incubated at 23° C. for 60 minutes. Plates are read on Perkin Elmer Envision 2104 instrument in TR-FRET mode using a 340 nm excitation filter, 520 nm fluorescence emission filter, and 490 or 495 nm terbium emission filter.

Several of a compound disclosed herein were tested according to the above methods and found to exhibit an LRRK2 G2019S $IC_{50}$ as indicated in Table 3.

Biological Example 2

Metabolic Stability

Metabolic stability of select compounds was evaluated in human liver microsomes (from Corning or XenoTech, LLC) using a 96-well plate assay format. Compounds were incubated at 37° C. at 1 μM final concentration in the microsomal matrix (0.5 mg/mL total protein) in the presence or absence of NADPH cofactor. An NADPH regenerating system, comprised of NADP, $MgCl_2$, isocitric acid, and isocitrate dehydrogenase, was used in the assay. Enzymatic reactions were conducted for 0, 5, 10, 20, 30, or 60 min before termination by addition of acetonitrile containing tolbutamide and labetalol internal standards (100 ng/mL). After shaking for 10 min, plates were subjected to centrifugation (4000 rpm at 4° C.) for 20 min and supernatants mixed 1:3 with HPLC grade water. Samples were analyzed by LC-MS/MS using appropriate MRM transitions for each analyte and internal standard (IS). Analyte/IS peak area ratios were used to determine percent compound remaining at each time point. Intrinsic clearance ($Cl_{int}$; expressed as $mL \cdot min^{-1} \cdot mg^{-1}$) was calculated from the first order elimination constant (k, $min^{-1}$) of test article decay and the volume of the incubation. These values were scaled to intrinsic organ clearance ($Cl_{int}$) using human specific scaling factors (48.8 mg microsomal protein per g liver; 25.7 g liver per kg body weight). Organ $Cl_{int}$ was subsequently converted to hepatic clearance, HLM, ($CL_{hep}$, mL·min-1·kg-1) using the well-stirred model of hepatic elimination, where $Q_h$ is human hepatic blood flow (20.7 mL·min-1·kg-1).

$$CL_{hep} = \frac{Q_h * CL_{int}}{(Q_h + CL_{int})}$$

$CL_{hep}$ is the projected human clearance in the liver based on the above in vitro assay. A lower value is indicative of less compound being removed by the liver. Data for compounds tested in this assay is shown in Table 3.

Biological Example 3

MDR1-MDCK Permeability

The blood brain barrier (BBB) separates circulating blood from the extracellular fluid of the central nervous system (CNS). The passive membrane permeability (Papp) and MDR1 (P-glycoprotein) substrate efflux potential are determined using the MDR1-MDCK cell line as an in vitro model of the effective permeability of a compound through the BBB. A bidirectional assay was conducted in pre-plated MDR1-MDCK cells using a 12 or 96-well plate in the absence or presence of MDR1 inhibitor (GF120918 or Valspodar). Assays were run in duplicate in transport buffer (HBSS, pH 7.4) for 90 or 120 min (minutes) at 37° C., using a test article concentration of 1 μM. Monolayer integrity was confirmed using Lucifer yellow, and appropriate positive controls for passive permeability and MDR1 transport were included in each experiment. Following incubation, samples from donor and receiver compartments are removed and quenched with acetonitrile containing an appropriate internal standard (IS). Protein was precipitated by centrifugation for 10 min at 3220 g, and supernatants diluted in ultra-pure water (if necessary) prior to analysis by LC-MS/MS using appropriate MRM transitions for analytes and IS. Papp (apparent permeability expressed in cm/sec [centimeter/second]) values were calculated according to the following equation:

$$P_{app}\ (\text{cm/sec}) = \frac{dC_R}{dt} \times \frac{V_R}{(\text{Area} \times C_A)} \text{ or } \frac{V_R}{\text{Area} \times \text{Time}} \times \frac{C_R}{C_o}$$

where $V_R$ is the solution volume in the receiver chamber (apical or basolateral side), Area is the surface area for the insert membrane), Time is incubation time expressed in seconds, $C_R$ is the peak area ratio (analyte/IS) in the receiver chamber, $C_A$ is the average of the initial and final concentrations in the donor chamber, and $C_o$ is the initial peak area ratio in the donor chamber. $P_{app}$ was determined in both the apical to basolateral (A→B) and basolateral to apical (B→A) directions.

Monolayer efflux ratios (ER) were derived using the following equation:

$$ER = \left[\frac{P_{app}\ (B \to A)}{P_{app}\ (A \to B)}\right]$$

Compounds with an MDR1-MDCK efflux ratio of less than or equal to five are likely to demonstrate ability to cross the blood-brain-barrier. Compounds with an MDR1-MDCK efflux ratio above 20 are not expected to cross the blood brain barrier. Data for compounds tested in this assay is shown in Table 3.

Biological Example 4

Inhibition of pSer935 in HEK293 Cells with Expressed G2019S LRRK2

This assay shows test compound inhibitory activity of the auto phosphorylation of LRRK2 as a direct marker of kinase inhibition.

LRRK2 encodes a multi-domain protein containing a GTPase domain, kinase domain, and several potential protein-protein interaction domains. The majority of identified pathogenic mutations in LRRK2 are located within its catalytic domains, including the most common mutation associated with LRRK2 (G2019S, as well as N2081D). These mutations are reported to increase LRRK2's kinase activity, either through direct mutations within the kinase domain itself or through indirect mechanisms. Increased kinase activity has been proposed to contribute to LRRK2-mediated pathogenesis, supporting the therapeutic potential of compounds disclosed herein.

Phosphorylation of LRRK2 at residue serine 935 (pS935) is a well-established biomarker of kinase activity that has been previously demonstrated to be sensitive to pharmacological inhibition of LRRK2 kinase activity, and can be detected at endogenous levels in cells and tissues. Treatment with small molecule kinase inhibitors has been shown to rapidly dephosphorylate Ser935 after inhibition of LRRK2. In this assay, inhibition of phosphorylation of LRRK2 at residue serine 935 (pS935) by test compound was determined in HEK293 cells.

HEK293 cells were first transiently transfected with a plasmid harboring FLAG-tagged human LRRK2 cDNA with G2019S mutation (p.G2019S) under the control of CMV promoter for robust overexpression. The levels of phosphorylated Ser935 in G2019S expressing cells with or without compound treatment were measured by MSD using an anti-FLAG capture antibody and a phosho-specific anti-LRRK2 pS935 monoclonal detection antibody. The $IC_{50}$ was determined by fitting a 10-point dose response data in duplicate with four parameter non-linear regression curve.

Materials:

| Name | Vendor code |
|---|---|
| Cell line: 293T | ATCC ® CRL-11268 ™ |
| DMSO | Fisher D128-500 |
| Protease Inhibitor (100X stock) | Sigma-P8340 |
| Phosphatase Inhibitor (100X stock) | Sigma-P0044 |
| DMEM cell culture medium | Invitrogen-11965118 |
| FBS | MinHai-SA10 |
| Penn Strep | Hyclone-SV30010 |
| GlutaMax-I | Invitrogen-35050079 |
| Block bufffer | LiCor-927-40000 |
| Anti-pSer935 LRRK2 antibody | Abcam-133450 |
| Sulfo-tag goat anti-rabbit Ab | R32AB-1 |
| 4X MSD read buffer | MSD-R92TC-1 |
| Monoclonal ANTI-FLAG, M2 antibody | Sigma-F3165 |
| Cell culture dish | Corning-430599 |
| 96 well cell culture plates | Corning-3599 |
| MSD high binding plate | MSD-L15XB-3 (96 wells)<br>MSD-L21XB-4 (384 wells) |
| Compound dilution plate | Agilent-5042-1385 |
| Compound transfer tips | Apricot-125-96R-EZ-S |
| MSD Sector reader | MSD6000 |

Test Protocol:

(Day 1) 293T cell seeding: 293T cells were seeded ($1.4\times10^6$/well) into each well of a 6-well plate. After two days in culture, the cell number can grow into $5\times10^6$/well, so N+1 wells were seeded (enough for N 96 well assay plates).

(Day 2) 293T cell transfection: 5 μL of pCMV-FLAG-G2019S or pCMV-FLAG-WT LRRK2 (0.5 μg/μL) was added into 145 μL of DMEM medium, and mixed thoroughly by pipette up and down several times. 15 μL of SuperFect Transfection Reagent was added into samples, mixed thoroughly by pipetting up and down several times, and allowed to equilibrate at room temperature for 5-10 minutes. 0.5 mL of pre-warmed cell culture medium was added into samples, and mixed thoroughly by pipetting up and down several times. 650 μL of the mixture was added dropwise into each well of the 6 well plate, the plate was swirled to mix thoroughly, and incubated in a 37° C. incubator with a humidified atmosphere of 5% $CO_2$ for 20-24 hours.

(Day 3) 293T cells seed into 96 well plates: Cells were harvested and resuspended in cell culture medium at $0.96\times10^6$ cells/mL density. 50 μL/well cells were plated onto 96-well cell culture plate (48,000 cells/well), and the plates were incubated in a 37° C. incubator with a humidified atmosphere of 5% $CO_2$ for 20-24 hours.

(Day 4) Inhibitor Treatment and Cell Lysis: The compound destination plates were thawed at room temperature and centrifuged at 2000 rpm. 55 μL cell culture medium was added into compound destination plate, and the plate was warmed at 37° C.

50 μL of cell culture medium containing compounds was transferred into cell culture plate. Plates were incubated in a 37° C. incubator with a humidified atmosphere of 5% $CO_2$ for 90 minutes, after which all of compound-containing medium was completely aspirated manually with 300 μL pipette. 100 μL/well of Lysis Buffer was added and the plates sealed, shaken at 4° C. for 30 minutes, and stored at −20° C. until usage.

(Day 5) MSD procedure: 2 μg/25 μL/well of FLAG antibody diluted in PBS was added into the MSD plate, incubated for two hours at room temperature or overnight at 4° C. (in Day 4). 50 μL (3.9 μg/μL) of FLAG antibody plus 2.5 mL PBS, per 96 well plate, or 50 μL (3.9 μg/μL) anti-FLAG antibody plus 5 mL PBS per 384 well plate. The plates were centrifuged at 1000 rpm for 10 seconds and shaken with a plate shaker for 10 seconds.

Anti-FLAG antibody was discarded, and the wells were washed using multidrop, low speed, two times with 300 μL/well of wash buffer for a 96 well plate or three times with 70 μL/well of wash buffer for a 384 well plate. 50 μL/well of block buffer for a 96 well plate, or 25 μL/well of block buffer for a 384 well plate, was added and the plates were incubated for two hours at room temperature. The Block buffer was then discarded and the wells washed two times using multidrop, low speed, with 300 μL/well of wash buffer for a 96 well plate, or three times with 70 μL/well of wash buffer for a 384 well plate.

25 μL of cell lysate was transferred into a 96 well MSD plate, or 12.5 μL of cell lysate into 384 well MSD plate, and the plates were incubated for one hour at room temperature.

Note: The cell lysate should be thawed one hour prior to this step, the plate centrifuged at 1000 rpm for one minute, shaken for 30 seconds, and then unsealed for lysate transfer.

The lysate was then discarded and the wells washed three times using multidrop, low speed, with 300 μL/well of wash buffer for a 96 well plate, or four times with 70 μL/well of wash buffer for a 384 well plate.

Anti-LRRK2 pS935 antibody was diluted (1:200) in blocking buffer, added to each well (25 μL/well antibody into 96 well plate, 12.5 μL/well antibody into 384 well plate), and the plate was incubated at room temperature. After one hour, the antibody was discarded and the wells were washed with wash buffer using multidrop, low speed; three times with 300 μL/well of wash buffer for a 96 well plate, or four times with 70 μL/well of wash buffer for a 384 well plate.

SULFO-tagged goat anti-rabbit antibody was diluted (1:500) with blocking buffer, added to each well (25 μL/well antibody into 96 well plate, 12.5 μL/well antibody into 384 well plate), and the plate was incubated at room temperature. After one hour, the antibody was discarded and the wells were washed with wash buffer using multidrop, low speed; three times with 300 μL/well of wash buffer for a 96 well plate, or four times with 70 i/well of wash buffer for a 384 well plate. The final wash buffer aliquot was not removed until read buffer was added.

Read buffer was freshly prepared (1:1 dilution of 4× reading buffer with MilliQ water), and light protected. Wash buffer was then removed and 150 μL/well of 2× read buffer was added into each well (96 well plate), or 50 μL/well of 2× read buffer into each well (384 well plate). The plates were then incubated for three minutes and read within 15 minutes using a MSD Sector reader (MSD6000). Dotmatics was used for data analysis. Z factor >0.5. Assay window=3-6 folds. Percent inhibition rate was calculated as follows:

% inhibition rate=(treated samples−ZPE)/(HPE−ZPE)*100

Data for compounds tested in this assay is shown in Table 3.

TABLE 3

| Example No. | | LRRK2 G2019S TR-FRET (nM) | HEK293T LRRK2 G2019S pS935 (nM) | HLM Avg mL/min/kg | MDCK-MDR1 Efflux Avg |
|---|---|---|---|---|---|
| 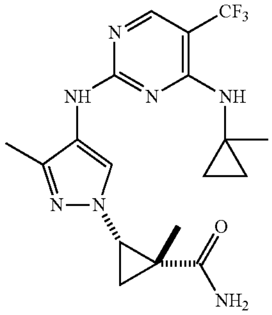 | 1 | 1.03 | 1.79 | 6.4 | |
| 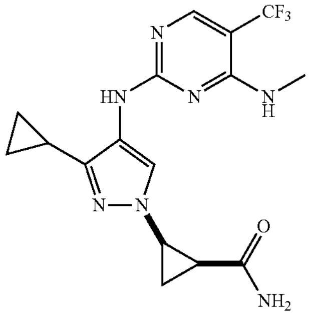 | 2 | 2.8 | 3.06 | | |
| 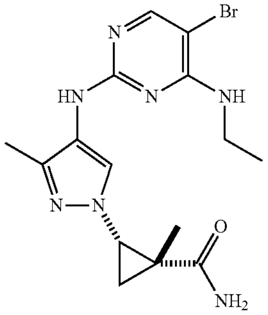 | 3 | 2.28 | 10.5 | | |
| 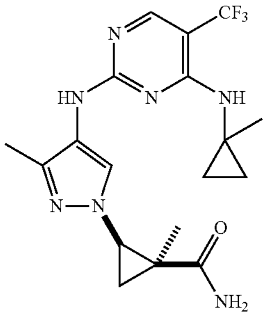 | 4 | 1.49 | 3 | 8.9 | |

TABLE 3-continued
| Example No. | | LRRK2 G2019S TR-FRET (nM) | HEK293T LRRK2 G2019S pS935 (nM) | HLM Avg mL/min/kg | MDCK-MDR1 Efflux Avg |
|---|---|---|---|---|---|
| 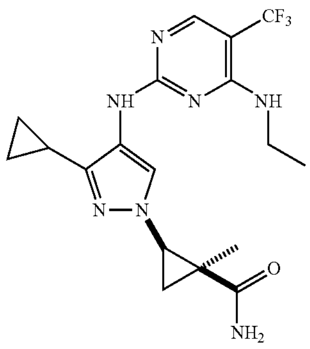 | 5 | 0.92 | 5.12 | 11 | |
| 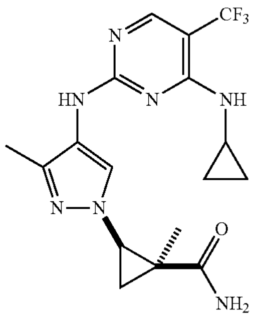 | 6 | 1.23 | 5.79 | | |
| 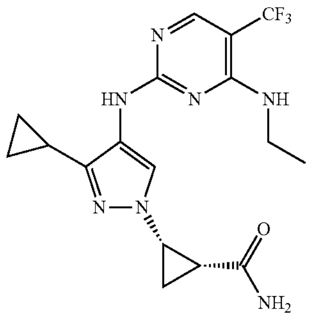 [SMILES: CCNc1nc(Nc2cn([C@H]3C[C@H]3C(N)=O)nc2C2CC2)ncc1C(F)(F)F] | 7 | 1.47 | 1.83 | 3.6 | 110 |
| 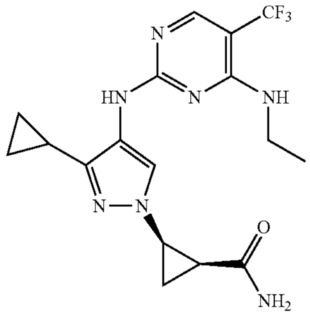 [SMILES: CCNc1nc(Nc2cn([C@@H]3C[C@@H]3C(N)=O)nc2C2CC2)ncc1C(F)(F)F] | 8 | 1.11 | 4.94 | | |

TABLE 3-continued

| Example No. | LRRK2 G2019S TR-FRET (nM) | HEK293T LRRK2 G2019S pS935 (nM) | HLM Avg mL/min/kg | MDCK-MDR1 Efflux Avg |
|---|---|---|---|---|
| Comparative Example A 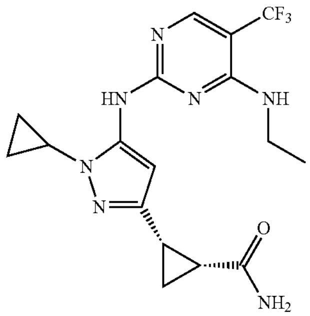 | 1.41 | 11.8 | 2.6 | 144 |

The $IC_{50}$ values from the cellular assay of Biological Example 4 (HEK293T LRRK2 G2019S pS935) are generally ten times greater than the values from the biochemical assay of Biological Example 1 (LRRK2 G2019S TR-FRET), with the tenfold difference decreasing as the $IC_{50}$ values approach 10 nM or less. At single digit nanomolar $IC_{50}$ concentrations, the cellular assay was found to have greater sensitivity than the biochemical assay, and thus more accurately resolves the relative $IC_{50}$ values of compounds in this range.

As shown in the table above, Compounds 1-8 were surprisingly found to be more active LRRK2 inhibitors than Comparative Example A when tested according to the cellular assay of Biological Example 4.

Compounds 1-8 are expected to be P-glycoprotein (P-gp) substrates and have very poor brain penetration (Hitchcock, J. Med. Chem. 2012, 55, 4877-4895) based on their calculated total polar surface area of 110 (Ertl et al., J. Med. Chem. 2000, 43, 3714-3717). Compound 7 was further tested in vitro (Biological Example 3, MDR efflux assay) and was found to be a clear P-gp substrate (efflux ratio=110) suggesting very poor brain penetration. Thus compounds 1-8 would be advantageous in avoiding CNS related side effects in the treatment of non-CNS diseases as compared to LRRK2 inhibitors that can cross the blood brain barrier.

In particular, Compound 7 was surprisingly found to be a highly potent, stable, and non-brain penetrant LRRK2 inhibitor. Compound 7 was found to be approximately 11.8/1.83 times more potent than Comparative Example A.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms “comprising”, “including,” “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:
1. A compound selected from:
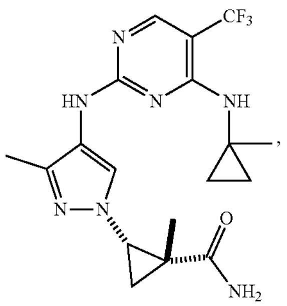
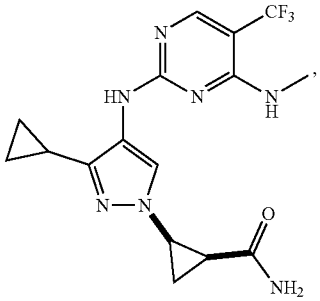
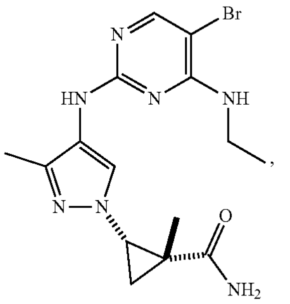
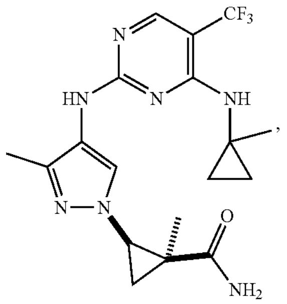
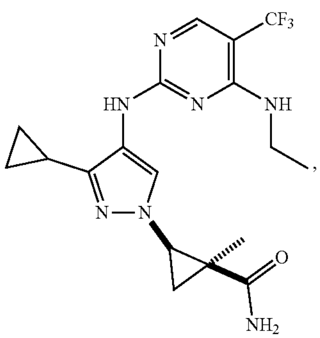
-continued
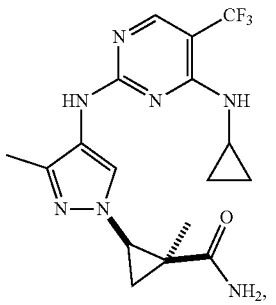
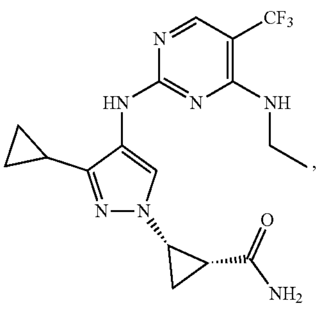
and
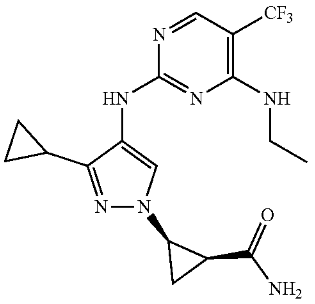
or a pharmaceutically acceptable salt, stereoisomer, or a mixture of stereoisomers thereof.
2. A compound having the structure:
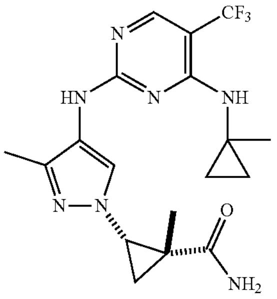
or a pharmaceutically acceptable salt thereof.

3. A compound having the structure:

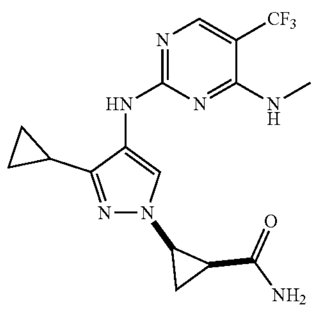 [SMILES: CNc1nc(Nc2cn([C@@H]3C[C@@H]3C(N)=O)nc2C2CC2)ncc1C(F)(F)F]

or a pharmaceutically acceptable salt thereof.

4. A compound having the structure:

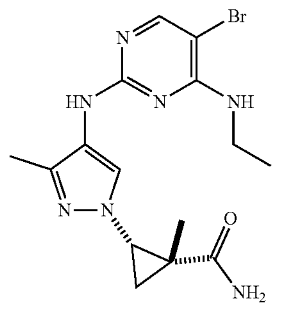 [SMILES: CCNc1nc(Nc2cn([C@H]3C[C@@]3(C)C(N)=O)nc2C)ncc1Br]

or a pharmaceutically acceptable salt thereof.

5. A compound having the structure:

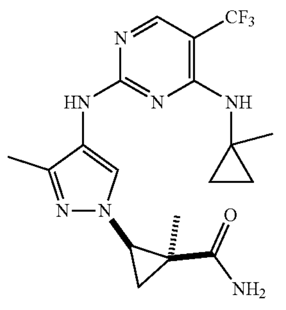

or a pharmaceutically acceptable salt thereof.

6. A compound having the structure:

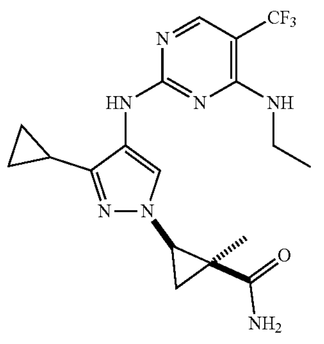 [SMILES: CCNc1nc(Nc2cn([C@@H]3C[C@]3(C)C(N)=O)nc2C2CC2)ncc1C(F)(F)F]

or a pharmaceutically acceptable salt thereof.

7. A compound having the structure:

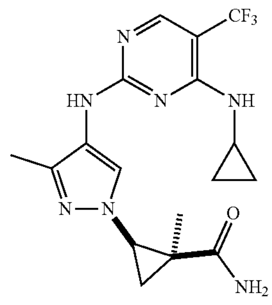 [SMILES: Cc1nn([C@@H]2C[C@]2(C)C(N)=O)cc1Nc1ncc(C(F)(F)F)c(NC2CC2)n1]

or a pharmaceutically acceptable salt thereof.

8. A compound having the structure:

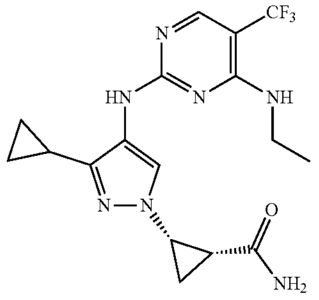 [SMILES: CCNc1nc(Nc2cn([C@H]3C[C@H]3C(N)=O)nc2C2CC2)ncc1C(F)(F)F]

or a pharmaceutically acceptable salt thereof.

9. A compound having the structure:

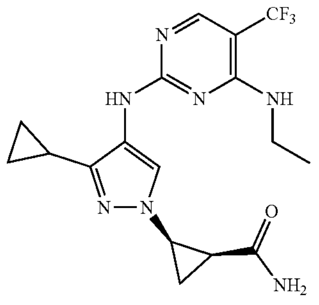 [SMILES: CCNc1nc(Nc2cn([C@@H]3C[C@@H]3C(N)=O)nc2C2CC2)ncc1C(F)(F)F]

or a pharmaceutically acceptable salt thereof.

10. A pharmaceutical composition comprising a compound claim 1, or a pharmaceutically acceptable salt, isotopically enriched analog, tautomer, stereoisomer, mixture of stereoisomers, or prodrug thereof, and a pharmaceutically acceptable carrier, diluent, or excipient.

11. A method for treating a disease or condition mediated, at least in part, by LRRK2, the method comprising administering an effective amount of the pharmaceutical composition of claim 10 to a subject in need thereof.

12. The method of claim 11, wherein the disease or condition is a cancer.

13. The method of claim 12, wherein the cancer is kidney cancer, breast cancer, prostate cancer, blood cancer, papillary cancer, lung cancer, acute myelogenous leukemia, or multiple myeloma.

14. The method of claim 11, wherein the disease or condition is an inflammatory disease.

15. The method of claim 14, wherein the inflammatory disease is leprosy, Crohn's disease, inflammatory bowel disease, ulcerative colitis, amyotrophic lateral sclerosis, rheumatoid arthritis, or ankylosing spondylitis.

16. The method of claim 14, wherein the inflammatory disease is Crohn's disease.

17. The method of claim 11, wherein the disease is a neurodegenerative disease.

18. The method of claim 17, wherein the disease is Parkinson's disease.

* * * * *